US005965379A

United States Patent [19]
Tamarkin et al.

[11] Patent Number: 5,965,379
[45] Date of Patent: *Oct. 12, 1999

[54] METHOD FOR MEASURING ENDOGENOUS CYTOKINES

[75] Inventors: Lawrence Tamarkin, Rockville; Giulio F. Paciotti, Baltimore, both of Md.

[73] Assignee: CytImmune Sciences Inc., College Park, Md.

[*] Notice: This patent is subject to a terminal disclaimer.

[21] Appl. No.: 08/959,267

[22] Filed: Oct. 28, 1997

Related U.S. Application Data

[63] Continuation of application No. 08/484,188, Jun. 7, 1995, abandoned, which is a continuation-in-part of application No. 08/331,333, Oct. 28, 1994, Pat. No. 5,587,294, which is a continuation of application No. 07/855,109, Mar. 20, 1992, abandoned, which is a continuation-in-part of application No. 07/732,867, Jul. 19, 1991, abandoned.

[51] Int. Cl.⁶ ................................................. G01N 33/533
[52] U.S. Cl. ..................... 435/7.93; 435/7.5; 435/7.9; 435/7.92; 435/7.95; 435/12; 435/14; 435/21; 435/26; 435/27; 435/28; 436/518; 436/523; 436/528; 436/538; 436/548; 436/808; 436/817
[58] Field of Search .................. 435/7.5, 7.9, 7.92–7.95, 435/12, 14, 21, 26, 27, 28; 436/518, 523, 528, 538, 548, 808, 817

[56] References Cited

U.S. PATENT DOCUMENTS

| Re. 31,006 | 8/1982 | Schuurs et al. . |
|---|---|---|
| Re. 32,696 | 6/1988 | Schuurs et al. . |
| 3,654,090 | 4/1972 | Schuurs et al. . |
| 3,839,153 | 10/1974 | Schuurs et al. . |
| 3,850,752 | 11/1974 | Schuurs et al. . |
| 4,016,043 | 4/1977 | Schuurs et al. . |
| 4,020,151 | 4/1977 | Bolz et al. . |
| 4,185,084 | 1/1980 | Mochida et al. . |
| 4,228,237 | 10/1980 | Hevey . |
| 4,271,140 | 6/1981 | Bunting . |
| 4,376,110 | 3/1983 | David et al. . |
| 4,486,530 | 12/1984 | David et al. . |
| 4,496,654 | 1/1985 | Katz et al. . |
| 4,594,326 | 6/1986 | Wade . |
| 4,798,207 | 1/1989 | Wade . |
| 4,863,726 | 9/1989 | Stevens et al. . |
| 5,137,805 | 8/1992 | Kingston . |
| 5,501,983 | 3/1996 | Lilja . |
| 5,587,294 | 12/1996 | Tamarkin . |

FOREIGN PATENT DOCUMENTS

| 0 071 976 | 4/1982 | European Pat. Off. . |
|---|---|---|
| 0 105 714 | 9/1983 | European Pat. Off. . |
| 0 232 717 | 1/1987 | European Pat. Off. . |
| 0 245 052 | 11/1987 | European Pat. Off. . |
| 93022359 | 2/1995 | WIPO . |

OTHER PUBLICATIONS

Cummins et al., "Protection of Calves Against Rhinovirus Infection by Nasal Secretion Interferon Induced by Infectious Bovine Rhinotracheitis," *American Journal of Veterinary Research*, vol. 41, pp. 161–165 (Jan. 1980).

Cummins et al., "Partial protection of calves against parainfluenza–3 virus infection by nasal–secretion interferon induced by infectious bovine rhinotracheitis virus," *American Journal of Veterinary Research*, vol. 43, No. 8., pp. 1334–1338 (Aug. 1982).

Todd et al., "Interferon in Nasal Secretions and Sera of Calves After Intranasal Administration of Avirulent Infectious Bovine Rhinotracheitis Virus: Association of Interferon in Nasal Secretions with Early Resistance to Challenge with Virulent Virus," *Infection and Immunity*, vol. 5, No. 5, pp. 699–706 (May 1972).

Kabashima et al., "Partial Characterization of an Interleukin–1–Like Factor in Human Gingival Crevicular Fluid from Patients with Chronic Inflammatory Periodontal Disease," *Infection and Immunity*, vol. 58, No. 8, pp. 2621–2627 (Aug. 1990).

Khan et al., "Human testis cytosol and ovarian follicular fluid contain high amounts of interleukin–1–like factor(s)," *Molecular and Cellular Endocrinology*, No. 58, pp. 221–230 (1988).

Wade et al., "Time–Integrated Measurementof Corticosteriods in Saliva by Oral Diffusion Sink Technology," *Clinical Chemistry*, vol. 37, pp. 1–7 (1991).

Charon et al., "Increased Thymocyte–Activating Factor in Human Gingival Fluid During Gingival Inflammation," *Infection and Immunity*, vol. 38, No. 3, pp. 1190–1195 (Dec. 1982).

Oppenheim et al., "Evidence for an In Vivo Inflammatory Role of Interleukin 1 (IL 1)," *Transplantation Proceedings*, vol. XIV, No. 3, pp. 553–555 (Sep. 1982).

Westacott et al., "Synovial fluid concentration of five different cytokines in rheumatic diseases," *Ann. Rheum. Dis.*, vol. 49(a), pp. 676–681 (1990).

Tamatani et al., "Existence of both IL–1a and β in normal human amniotic fluid: unique high molecular weight form IL–1β," *Immunology*, vol. 65, pp. 337–342 (1988).

Kimball et al., "Interleukin 1 Activity in Normal Human Urine," *The Journal of Immunology*, vol. 133, No. 1, pp. 256–260 (Jul. 1964).

Eastgate et al., "Correlation of Plasma Interlleukin 1 Levels with Disease Activity in Rheumatoid Arthritis," *The Lancet*, pp. 706–709 (Sep. 24, 1988).

Cannon et al., "Increased Plasma Interleukin–1 Activity in Women After Ovulation," *Science*, vol. 227, pp. 1247–1249 (Mar. 8, 1985).

(List continued on next page.)

*Primary Examiner*—Christopher L. Chin
*Assistant Examiner*—Bao-Thuy L. Nguyen
*Attorney, Agent, or Firm*—Jones & Askew, LLP

[57] ABSTRACT

The present invention relates to methods for measuring endogenous cytokines in blood. The method accurately measures the cytokines in the blood in the presence of substances that bind the cytokines thereby causing the measurement of the cytokines by conventional methods to give inaccurate results. The present invention also includes the non-invasive measurement of cytokines in biological fluids such as saliva and nasal secretions. Finally, the present invention allows one to monitor the level of cytokines in the blood during treatment of a human or animal with cytokines.

6 Claims, 14 Drawing Sheets

OTHER PUBLICATIONS

Maury et al., "Serum Immunoreactive Interlleukin–1 in Renal Transplant Recipients," *Transplantation Proceedings*, vol. XIX, No. 5, pp. 4349–4350 (Oct. 1987).

Cannon et al., "Endogenous Pyrogen Activity in Human Plasma After Exercise," Science, vol. 220, pp. 617–619 (May 6, 1983).

Waage et al., "The Complex Pattern of Cytokines in Serum From Patients with Meningococcal Septic Shock: Association between Interleukin 6, Interleukin 1, and Fatal Outcome," J. Exp. Med., vol. 169, pp. 333–338 (Jan. 1989).

Moldawer et al., "Circulating interleukin 1 and tumor necrosis factor during inflammation," The American Physiological Society, pp. R922–R928 (1987).

Miyai, "Enzyme Immunoassay System—Schematic Representation," Chapter IV, pp. 123–135.

Vilja et al., "A Rapid and Sensitive Non–Competitive Avidin–Biotin Assay for Lactoferrin," *Journal of Immunological Methods*, vol. 76, pp. 73–83 (1985).

Goldstein et al., "A competitive enzyme–linked immunoassay (ELISA) for the measurement of soluble human interleukin–2 receptors (IL–2R, Tac protein)," *Journal of Immunological Methods*, vol. 107, pp. 103–109 (1988).

Fucciillo, "Application of the Avidin–Biotin Technique in Microbiology," *BioTechniques*, vol. 3, No. 3, pp. 494–501 (1985).

Voller et al., "Enzyme immunoassays with special reference to ELISA techniques," *Journal of Clinical Pathology*, vol. 31, pp. 507–520 (1978).

Voller, The Enzyme Linked Immunosorbent Assay (ELISA), *Diagnostic Horizons*, vol. 2, No. 1, pp. 1–7 (Feb. 1978).

Jansson et al., "A biotin–labelled antigen radioimmunoassay (BILA) for antibodies to membrane antigens useful for monoclonal antibody screening," *Journal of Immunological Methods*, vol. 115, pp. 219–226 (1988).

Maldiney et al., "A biotin–avidin–based enzyme immunoassay to quantify three phytohormones: auxin, abscisic acid and zeatin–riboside," *Journal of Immunological Methods*, vol. 90, pp. 151–158 (1986).

Wagener et al., "Monoclonal antibodies for carcinoembryonic antigen and related antigens as a model system: determination of affinities and specificities of monoclonal antibodies by using biotin–labelled antibodies and avidin as precipitating agent in a solution phase immunoassay," *The Journal of Immunology*, vol. 130, No. 5, pp. 2302–2307 (May 1983).

Shiosaka et al., "A new method for producing a specific and high titre antibody against glutamate using colloidal gold as a carrier," *Brain Res.*, vol. 382, pp. 399–403 (1986).

Novick, et al., *Journal Exp. Med.*, vol. 170, pp. 1409–1414 (1989).

Honda et al., *The Journal of Immunology*, vol. 148, No. 7, pp. 2175–2180, (1992).

Fanslow et al., *Cytokine*, vol. 2, No. 6, pp. 398–401, (1990).

Novick et al., *Journal of Chromatography*, vol. 510, pp. 331–337, (1990).

Fanslow et al., *Science*, vol. 248, pp. 739–741 (1990).

Svenson et al., *Scand J. Immunol*, vol. 29, pp. 489–492 (1989).

Svenson et al., *Scand J. Immunol*, vol. 32, pp. 695–701 (1989).

Hansen et al., *Scand J. Immunol*, vol. 33, pp. 777–781 (1991).

Caruso et al., *The Journal of Immunology*, vol. 144, No. 2, pp. 685–690 (1990).

Cannon et al., *Lymphokine Research*, vol. 7, No. 4, 457–467 (1988).

Capper et al., *Cytokine*, vol. 2 No. 3, 182–189 (1990).

Mae et al., *Lymphokine Cytokine and Research*, vol. 10, No. 1, 61–68 (1991).

Interleukin 1β in Human Plasma: Optimization of Blood Collection, Plasma Extraction, and Radioimmunoassay Methods, Research Reports, vol. 7, No. 4, pp. 457–467 (1988).

Tumor Necrosis Factor (TNFa) Binding Protein: Interference in Immunoassays of TNAa, Kidney International, vol. 40, pp. 1166–1170 (1991).

Paciotti, G.F. et al., "Novel Enzyme Immunoassays for the Detection of the Cytokines Interleukin 1a and Interleukin 2 in the Circulation of Normal Subjects: 24–Hour Profiles," *Progress in NeuroEndocrinImmunology*, vol. 5, No. 1, pp. 21–30 (1992).

Mygind, N. et al., "Immunological Barriers in the Nose and Paranasal Sinuses," Acta Otolaryngol (Stockh), vol. 103, pp. 363–368 (1987).

Endres, E. et al., "In vitro production of IL1β, IL 1<<, TNF and IL2 in healthy subjects: distribution, effect of cyclooxygenase inhibition and evidence of independent gene regulation," Eur. J. Immunol., vol. 19, pp. 2327–2333 (1989).

Matsuda, T. et al., "Establishment of an interleukin 6(IL6)/B cell stimulatory factor 2–dependent cell line and preparation of anti–IL 6 monoclonal antibodies," Eur. J. Immunol., vol. 18, pp. 951–956 (1988).

Lisi, Peter J. et al., "Development and Use of a Radioimmunoassay for Human Interleukin–1β" *Lymphokine Research*, vol. 6, No. 3, pp. 229–244 (1987).

Michie, Hamish R. et al., "Detection of Circulating Tumor Necrosis Factor After Endotoxin Administration", *The New England Journal of Medicine*, vol. 318, No. 23, pp. 1481–1486 (Jun. 9, 1988).

Endres, Stefan et al., "Measurement of Immunoreactive Interleukin–1β from Human Mononuclear Cells: Optimization of Recovery, Intrasubject Consistency, and Comparison with Interleukin–1a and Tumor Necrosis Factor", *Clinical Immunology and Immunopathology*, vol. 49, pp. 424–438 (1988).

Paciotti, G.F. et al., "Determination of the 24–hour profiles of circulating IL–1–alpha and IL–2 levels in normals," *Lymphokine Research*, vol. 9, No. 4, pp. 594–595 (Oct. 1, 1990).

van der Meer, Jos W.M. et al., "Concentrations of Immunoreactive Human Tumor Necrosis Factor Alpha Produced by Human Mononuclear Cells in Vitro," *Journal of Leukocyte Biology*, vol. 43, pp. 216–223 (1988).

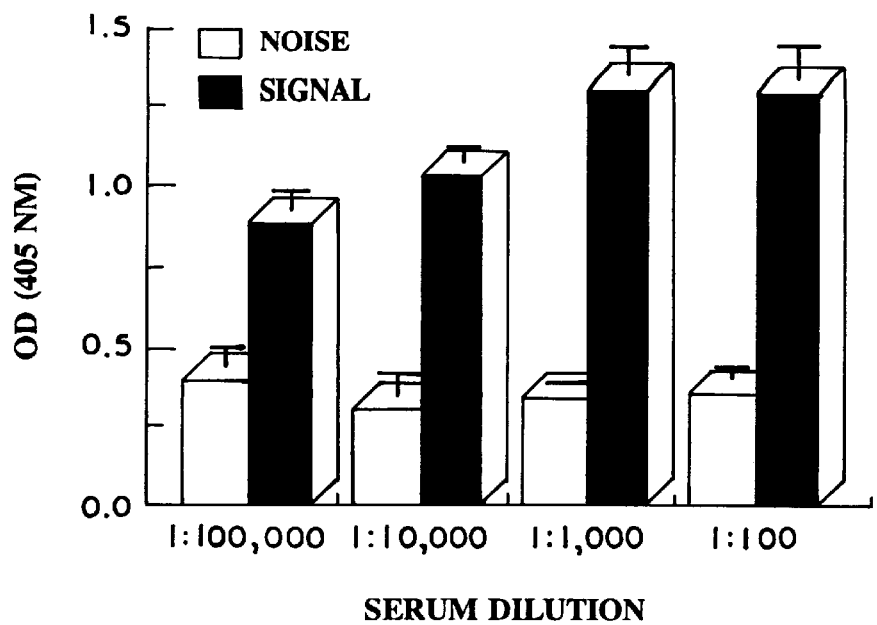
Fig_1
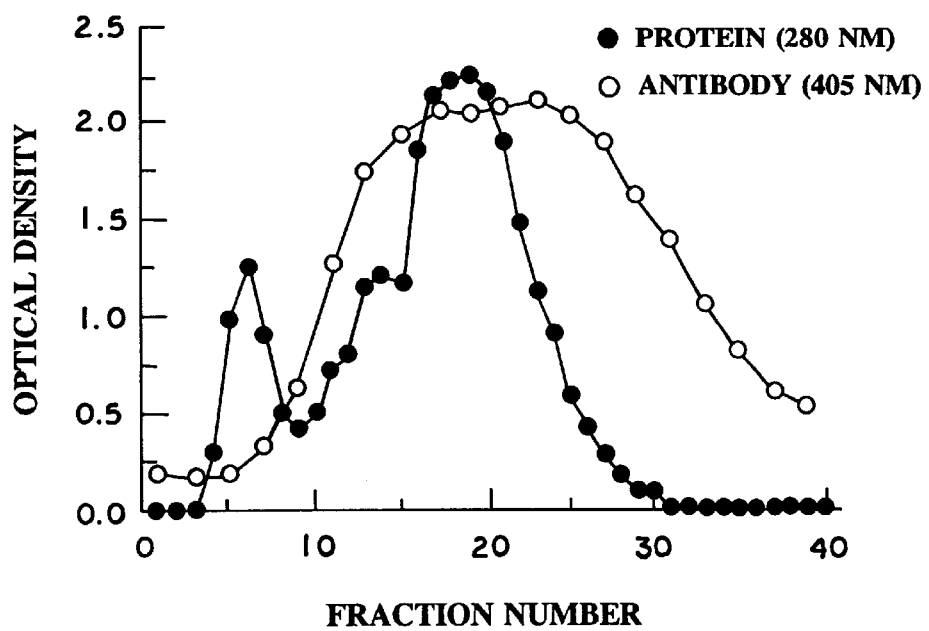
Fig_2

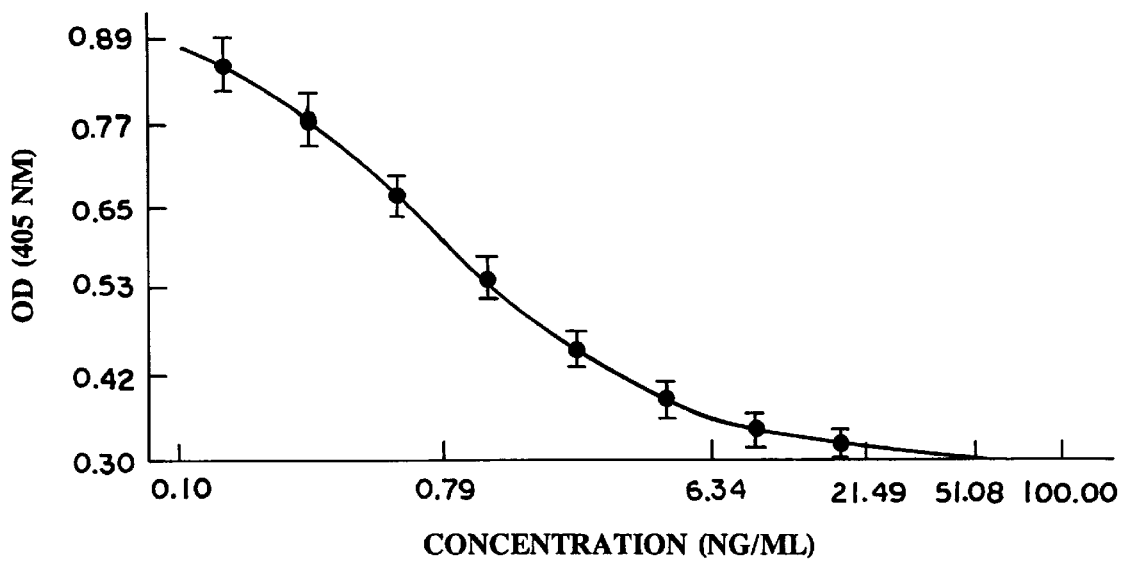
Fig_3
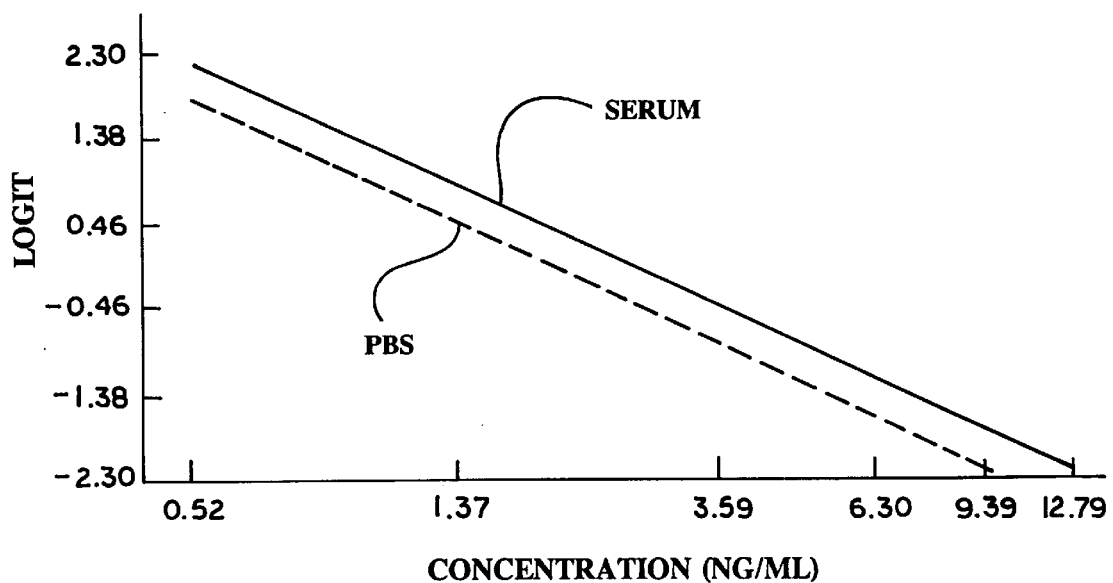
Fig_4

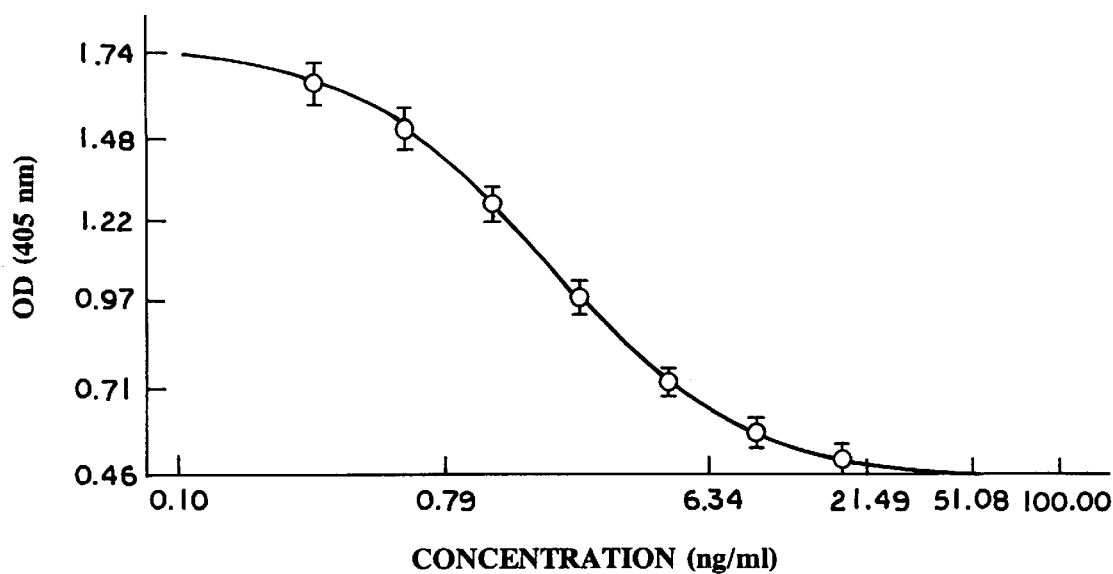
Fig_5
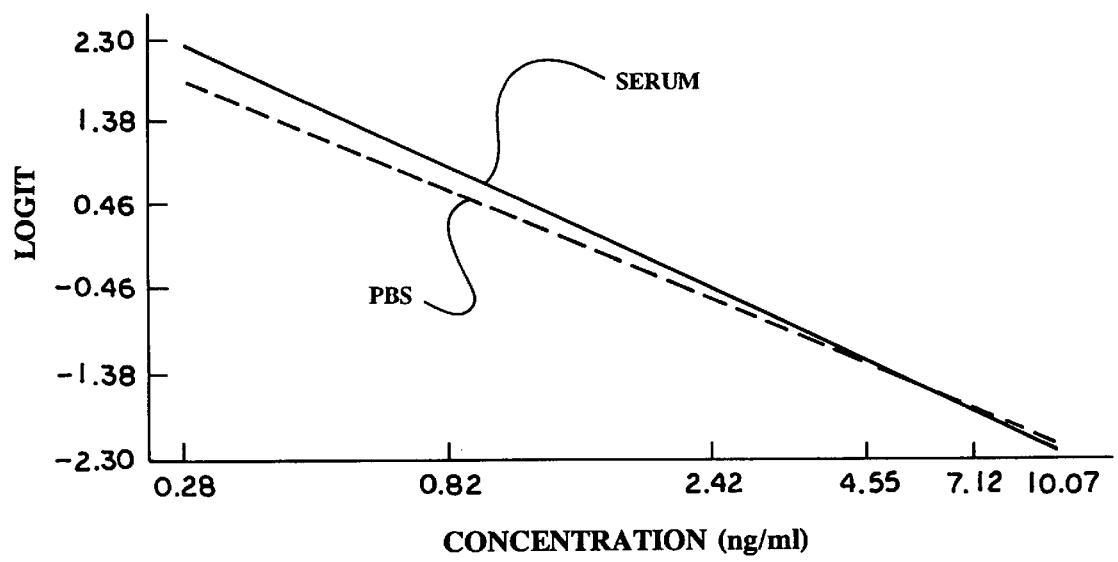
Fig_6

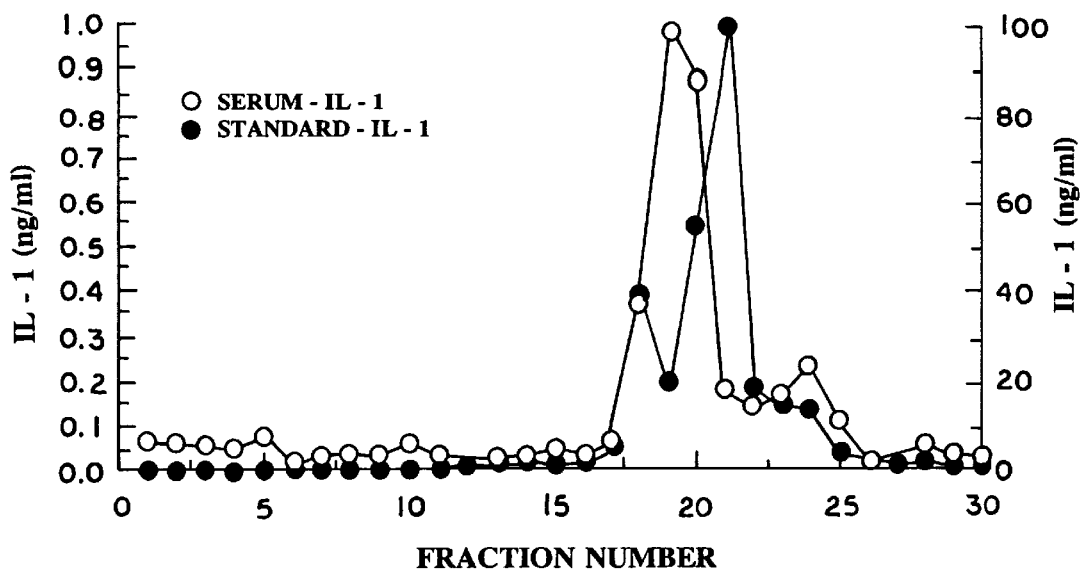
Fig_7A
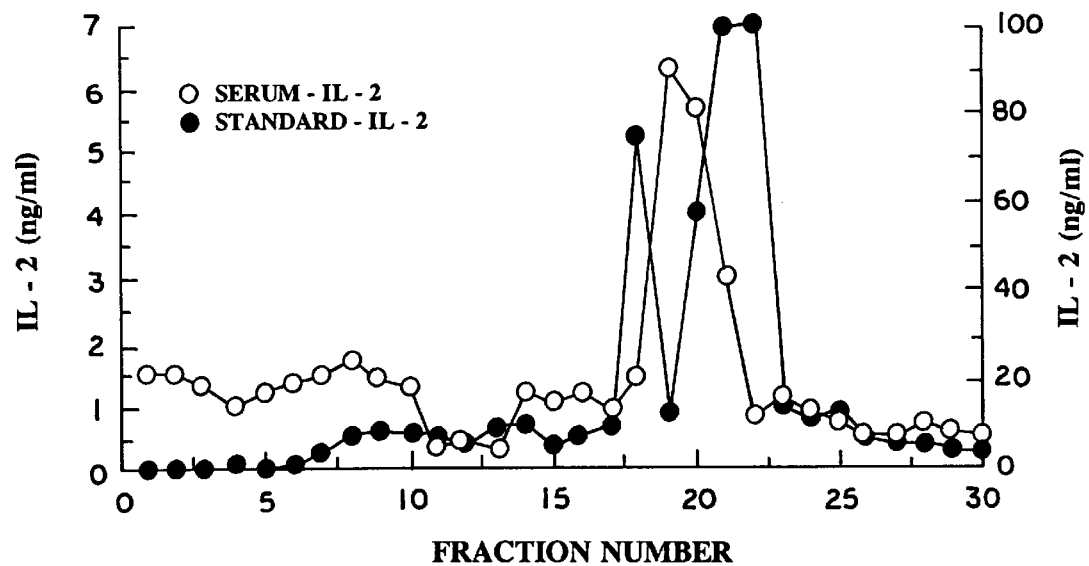
Fig_7B 1        2
MW
97,000 —
69,000 —
43,000 —
25,000 —
18,400 —  
14,300 —
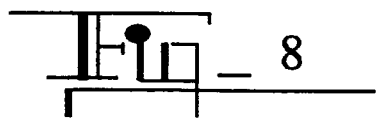

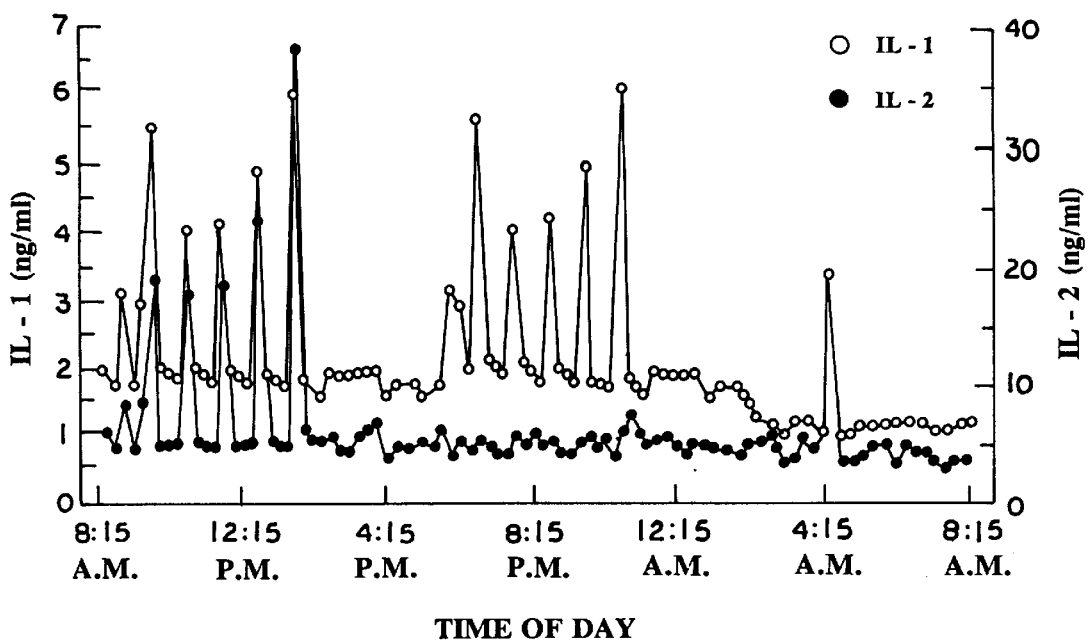
Fig_9A
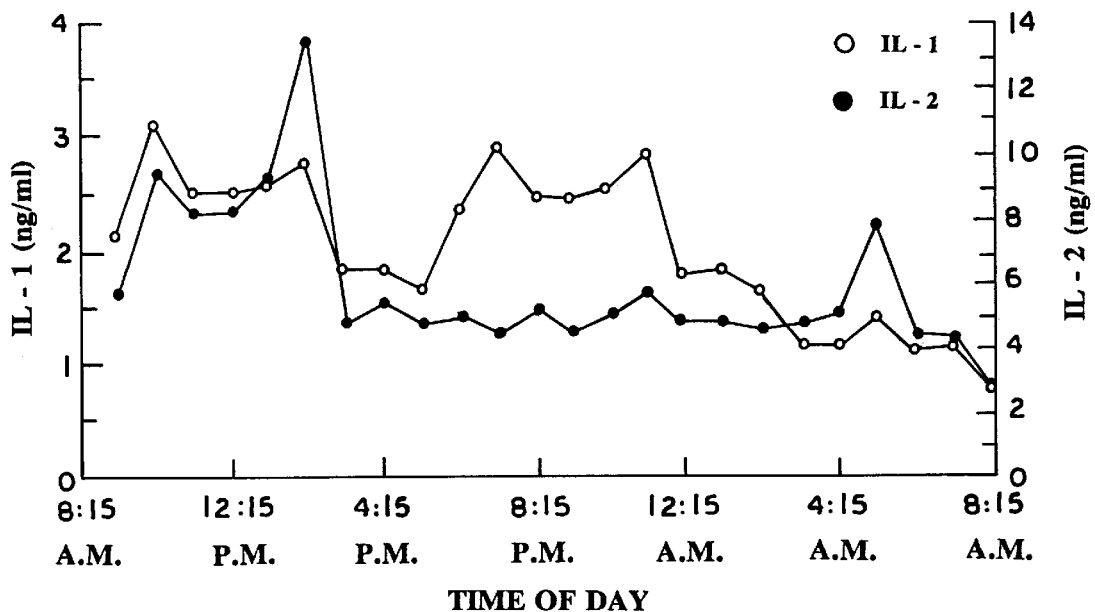
Fig_9B

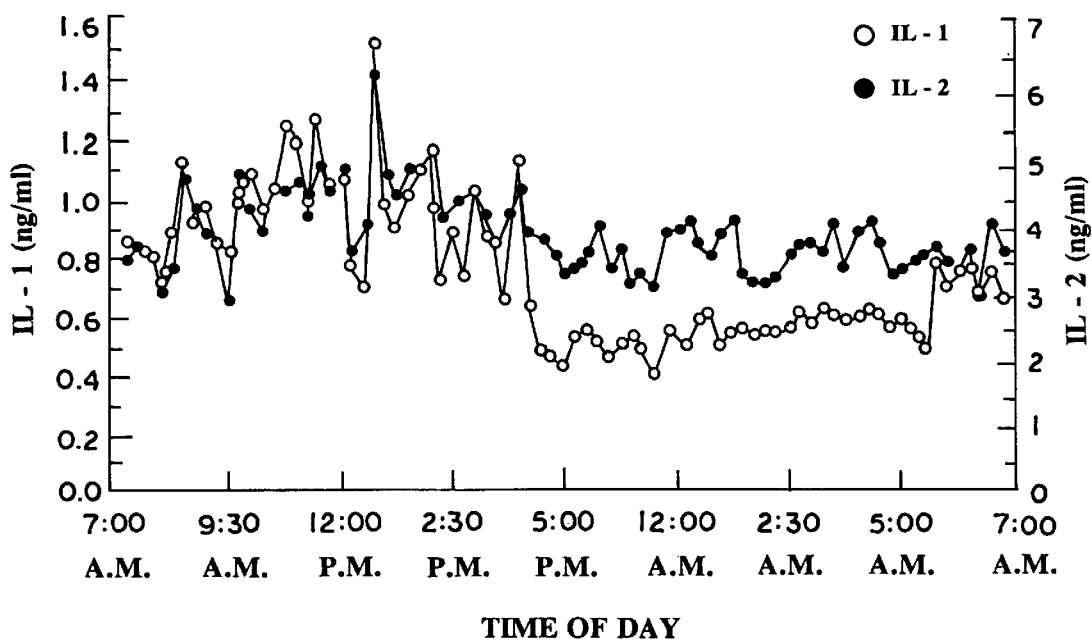
Fig_10A
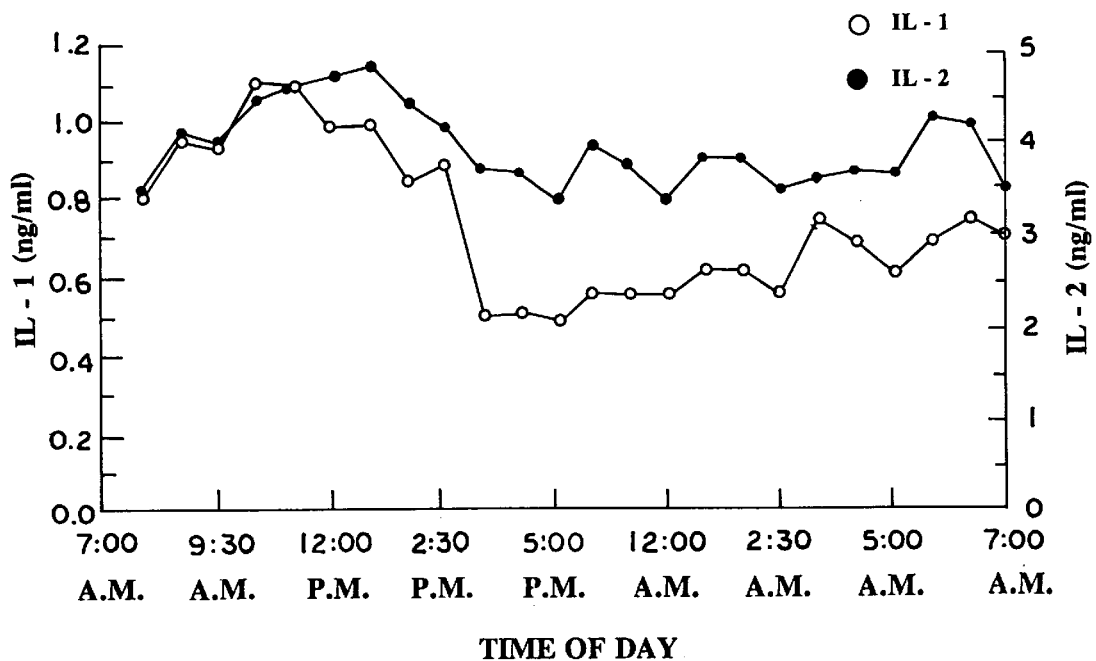
Fig_10B

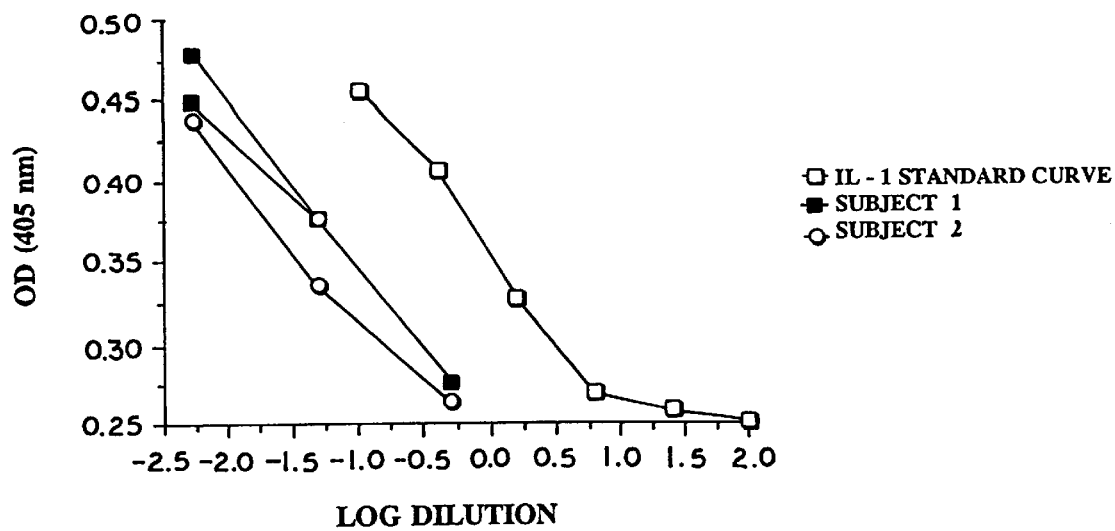
Fig_12
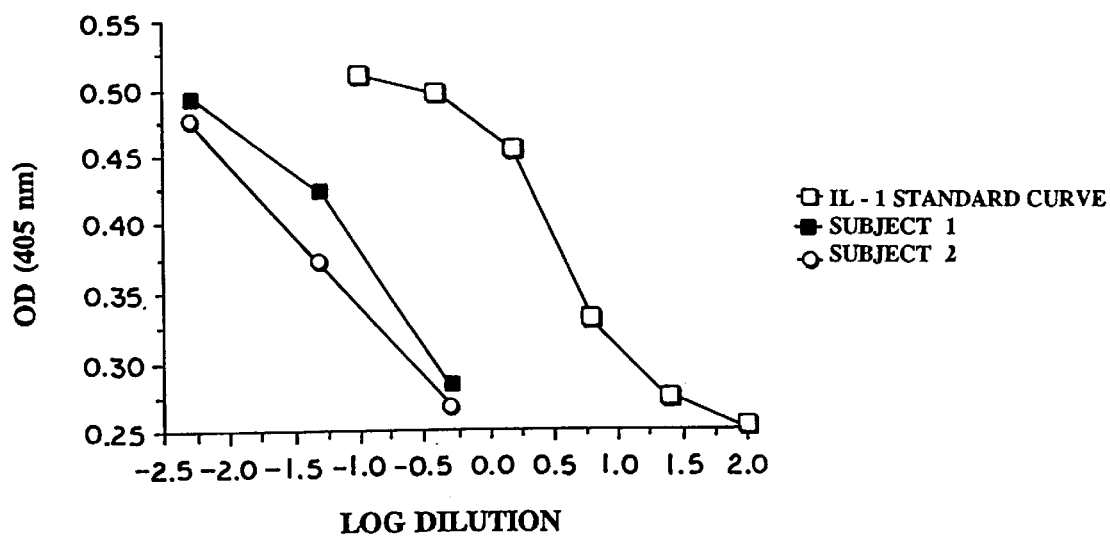
Fig_13

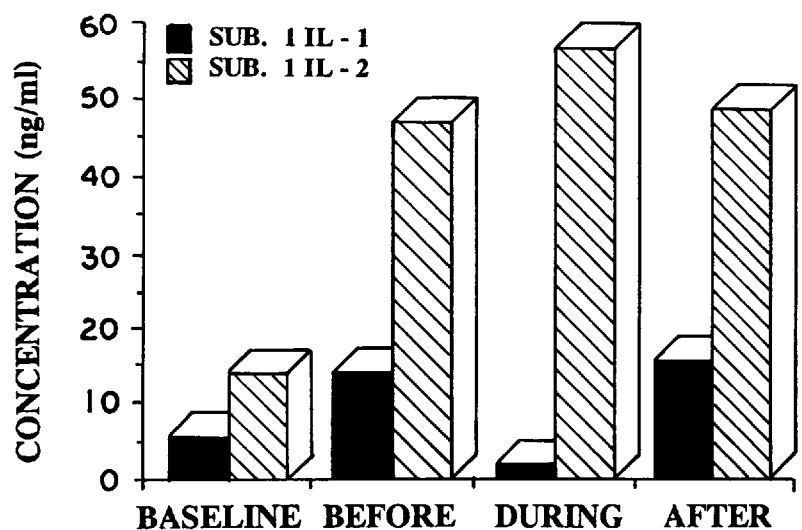
Fig_14
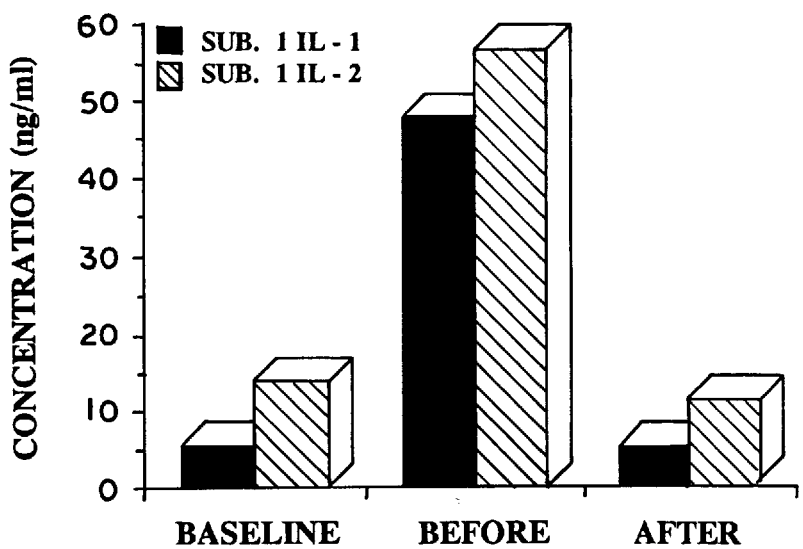
Fig_15

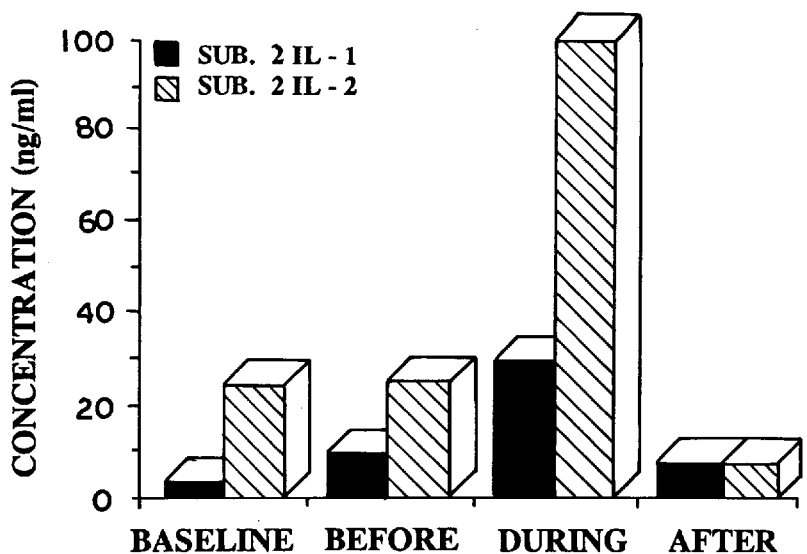
Fig_16
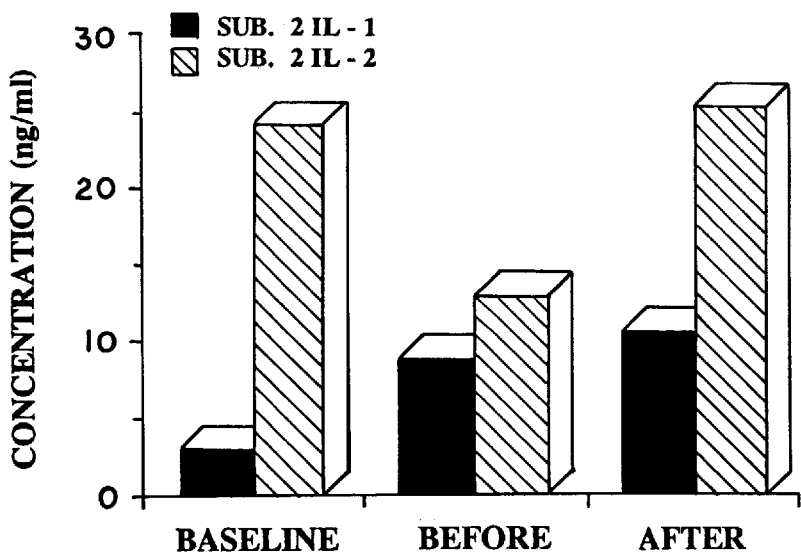
Fig_17

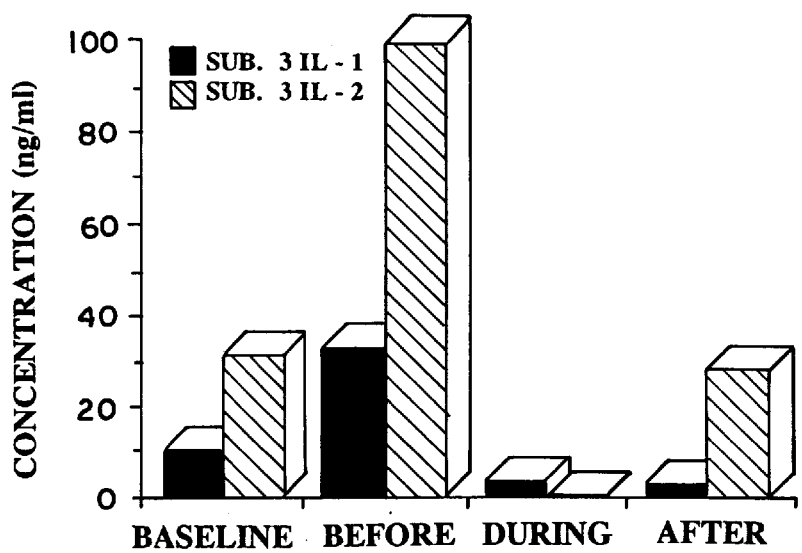
Fig_18
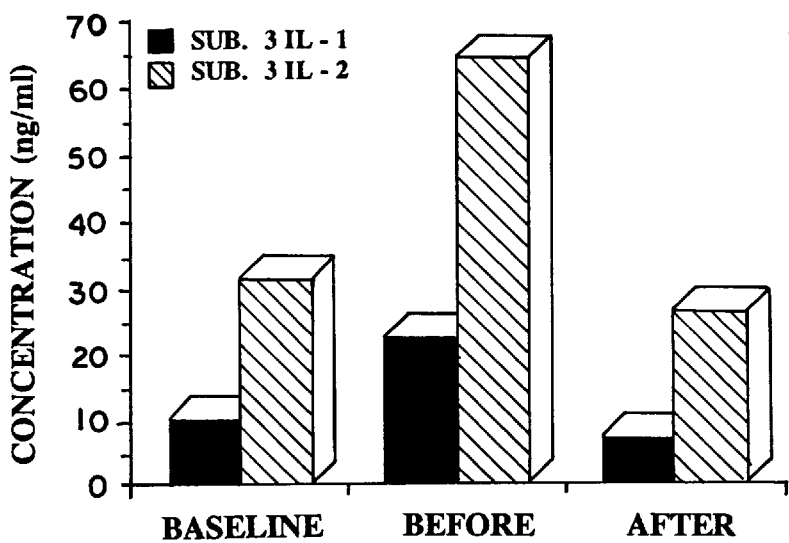
Fig_19

METHOD FOR MEASURING ENDOGENOUS CYTOKINES

CROSS-REFERENCE TO RELATED APPLICATIONS

This application is a continuation of U.S. patent application Ser. No. 08/484,188, filed Jun. 7, 1995 now abandoned, which is a continuation-in-part of U.S. patent application Ser. No. 08/331,333, filed Oct. 28, 1994, now U.S. Pat. No. 5,587,294, which is a continuation of U.S. patent application Ser. No. 07/855,109, filed Mar. 20, 1992, now abandoned, which is a continuation-in-part of U.S. patent application Ser. No. 07/732,867, filed Jul. 19, 1991, now abandoned.

FIELD OF THE INVENTION

The invention relates to methods for monitoring immunological function in a human or animal. More particularly, the present invention relates to accurately measuring the concentration of cytokines in the blood and other body fluids, including but not limited to, saliva, nasal secretions, tears and sweat.

BACKGROUND OF THE INVENTION

As used herein, the term "cytokine" is defined as growth factors secreted by immune or other cells, whose action is on cells of the immune system, such as, but not limited to, T-cells, B-cells, NK cells and macrophages. Representative cytokines include, but are not limited to, the group consisting of interleukin 1α, interleukin-1β, interleukin-2, interleukin-6, interferon-alpha, interferon-gamma, tumor necrosis factor-α, growth factors, such as TGFB, NGF, EGF, and oncogenes such as c-myc and c-fos. The term "EIA" means any immunoassay utilizing enzymes as the label. The term "endogenous cytokines" as used herein, means cytokines that are produced in vivo and normally circulate in the blood and various other biological fluids. The term includes prohormones which are larger molecular weight forms of cytokines which have not yet undergone post-transcriptional modification.

The impact of a variety of factors, including behavioral and environmental stress, on health and on susceptibility to diseases such as AIDS, cancer and autoimmune disease, is thought to be mediated by the immune system (Ader, R. et al., eds., PSYCHONEUROIMMUNOLOGY, Second Edition, Academic Press, New York (1991)). However, the effects of many of these influences on the function of the immune and host defense systems has been difficult to assess with certainty. This is due, in part, to the fact that most methods of evaluating the activity of the immune system focus on blood components, whether serum or cells.

A newly emerging field known as psychoneuroimmunology seeks to define, in a more mechanistic manner, the way in which biobehavioral factors are internally transduced to impact on the immune system and thereby influence susceptibility or resistance to a variety of pathological processes. Biobehavioral factors such as stress may be positive or negative risk factors for a pathologic outcome (Maier, S. F. et al., BRAIN BEHAV. IMMUN. 2: 8791 (1988)). It is thought by some researchers that a positive or negative attitude in humans may be a significant factor contributing to the overall host response in cancer, AIDS, or autoimmunity (see, for example, Ader et al., supra).

Our ability to evaluate and quantify discrete components of the immune system in a single individual over time (critical for monitoring the onset and/or treatment of diseases associated with AIDS, for example) has been elusive (Kiecolt et al., BRAIN BEHAV. IMMUN. 2: 67–78 (1988); Glaser, R. et al., BRAIN BEHAV. IMMUN. 1: 107–112 (1987)). The study of behavioral strategies that can be enlisted in the modulation of the immune system requires readily available analytical tools that can be used by a broad spectrum of investigators, including those not necessarily sophisticated in complex in vitro immunological techniques. Such methods are clearly lacking at present.

One method used widely in psychoneuroimmunology research is the stimulation of lymphocytes in vitro by mitogens, known also as lymphocyte blastogenesis or the lymphocyte transformation test (Maluish, A. E. et al., MANUAL OF CLINICAL LABORATORY IMMUNOLOGY (3rd Ed.), Rose, N. R., et al., (eds.), 274–281, (1986)). This method involves culture of lymphocytes separated from blood for several days in vitro in the presence of varying doses of mitogens. These mitogens are typically plant-derived or microorganism-derived non-specific activators of lymphocyte -proliferation. The ability of the cultured lymphocytes to incorporate $^3$H-thymidine (a well-known measure of DNA synthesis and cell growth) is generally used as a measure of the cells' response. This procedure is highly variable and technician-dependent, and is influenced by a number of unknown factors including the microenvironment provided by the subject's serum if incorporated in the assay.

In contrast to the more classic immunoassays for endocrine hormones, the absence of an established baseline response makes comparison between laboratories, and even within a laboratory, very difficult. However, the lymphocyte transformation test does provide functional information about the immune system because the test examines the response capacity of an entire class of cells, either T or B lymphocytes, depending upon the mitogen used. Unfortunately, the imprecision of the assay greatly diminishes its utility.

A second assay commonly used in psychoneuroimmunology research measures natural killer (NK) cell activity (Herberman, R. B., MANUAL OF CLINICAL LABORATORY IMMUNOLOGY (3rd Ed.), Rose, N. R., et al. (eds.), 308–314 (1986); Irwin, M. et al., BRAIN BEHAV. IMMUN. 1: 98–104 (1987); Jemmott, J. B. 3d, J. BEHAV. MED. 13: 53–73 (1990)). Again, this assay suffers from many of the shortcomings noted above. One reason this assay has become popular is the relative ease of its performance compared to most antigen-specific or antibody-dependent cellular cytotoxicity assays. However, compared to immunoassays commonly used for endocrine hormones, it still ranks as a rather difficult bioassay to perform.

The NK cell assay is based on the ability of a class of white blood cells to spontaneously lyse target cells, typically from an appropriately sensitive tumor cell line, which have been pre-labeled with $^{51}$Cr, thereby releasing the radioisotope into the medium. This assay lacks a quantifiable baseline, and comparisons between individuals is based on the differences in lysis effected by serial dilutions of a blood cell sample. The precise relationship between cells with NK function and the better known classes of leukocytes and lymphocytes is still unclear. Furthermore, the role of NK cells in immunological function and host defense to cancer or infectious disease is not firmly established.

A third approach to monitoring the immune system that has grown in popularity is the enumeration of lymphocyte subsets by flow cytometry using antibodies specific for cell-surface markers (Ault, K., MANUAL OF CLINICAL LABORATORY IMMUNOLOGY (3rd Ed.), Rose, N. R., et al., (eds.), 247–253 (1986)). This approach provides a snapshot of the distribution of various lymphocyte classes in the circulation, but does not provide functional information about any of the cells. Because many psychobiological studies involve a pre-treatment, treatment and post-treatment design, s the assay suffers from the disadvantage that some changes in cell numbers may be too rapid and transient to be meaningful. In contrast, the long-term status of circulating lymphocyte subsets may be too stable to provide an accurate measure of a response to a mild stimulus. The approach of enumerating subsets is thus more appropriate for examination of more permanent changes that occur in major medical illnesses, such as the loss of CD4$^+$ T cells in AIDS. Therefore, the utility of this method for measuring the response of the immune system to behavioral factors is limited.

A fourth approach, which has the distinct advantage of simple and non-stressful sampling, involves measurement of the secretory immunoglobulin, IgA, in the saliva (Johnson R. B., Jr. et al., J. IMMUNOASSAY 3: 73–89 (1982); Stone, A. A. et al., J. HUMAN STRESS 13: 136–140 (1987); Jemmott, J. B. 3d et al., BEHAV. MED. 15: 63–71 (1989); Jemmott, J. B. 3d et al., J. PERS. SOC. PSYCHOL. 55: 803–810 (1988); Jemmott, J. B. 3d et al., LANCET 1: 1400–1402 (1983)). The total concentration of salivary IgA reflects the presence of a large collection of antibodies of unknown antigen specificity. Furthermore, it is not clear how total IgA levels in saliva relate to the overall dynamics of the immune system. IgA antibodies are associated with mucosal surfaces and are thought to protect these surfaces from infection. Consequently, secretory IgA is found not only in saliva but also in tracheobronchial secretions, colostrum, milk and genitourinary secretions. The utility of monitoring secreted IgA as a useful index of activity of the immune system as a whole has been questioned (Stone et al., supra; Jemmott et al., supra).

Importantly, for testing behavioral factors, such as psychological stress on the immune system, it is particularly important to be able to sample a body fluid in a non-stressful manner. For example, obtaining a blood sample by venipuncture may itself induce physiological changes which could contaminate the data obtained. Thus, a method which would allow measurement of salivary levels of a cytokine or other product of the immune system would have several major advantages over existing approaches, such as (a) eliminating the risk and stress associated with phlebotomy; (b) serving as a window into the internal milieu; (c) allowing simple "at home" collection; (d) permitting a dynamic assessment over time; (e) providing an essential new tool for the evaluation of brain/immune system interactions; (f) serving as a measure which will assist in evaluating the impact of stress on health and (g) providing a measure that may be relevant to the onset of disease after initial pathogenic events, such as HIV infection in AIDS.

Two regulatory molecules of the immune system are interleukin 1 and 2 (IL-1 and IL-2). The ability of IL- 1 and IL-2 to modulate a cytokine "cascade" and the concomitant cell proliferation, differentiation and effector function of lymphoid cells has been characterized in detail (see, for example, Kampschmidt, R. F., J. LEUK. BIOL. 36: 341–355 (1984); Smith, K. A., ANN. REV. IMMUNOL. 2: 319–333 (1984)).

These two molecular signals are apparently not limited to action within the immune system, as recent studies indicate that both of these cytokines act as homeostatic regulators outside the immune system. For example, IL-1 has been shown to act as a potential modulator of the hypothalamic-pituitary-adrenal axis (Besedovsky, H. et al., SCIENCE 233: 652–654 (1986); Bernton, E. W. et al., SCIENCE 1987: 519–521 (1987)), while IL-2 has been shown to affect Leydig cell steroidogenesis (Gou, H. et al., ENDOCRINOLOGY 127: 1234–1239 (1990)). Studies have demonstrated that IL-1 and IL-2 directly (without the presence of macrophages or T-cells) inhibited the in vitro and in vivo growth of hormone-dependent human breast cancer cells (Paciotti, G. F. et al., MOL. ENDOCRINOL. 2: 459–464 (1988); Paciotti, G. F. et al., ANTICANCER RES. 8: 1233–1240 (1988); Paciotti, G. F. et al., ANTICANCER RES. 11: 25–32 (1991)). It appears, therefore, that these cytokines not only affect classical autocrine/paracrine loops within the immune system, but also affect endocrine circuits and may therefore modulate interactions between the endocrine and immune systems.

For IL-1 and IL-2 to play roles as "endocrine-like" hormones, they must exist in sufficient quantities to reach and affect their hypothesized target sites. Thus, ascertaining the biological basis of an endocrine action for such signal molecules traditionally thought to belong to the immune system, depends on our ability to detect and monitor, in a quantitative manner, the endogenous concentrations of these molecules. Conventional methods of measuring IL-1 and IL-2, as well as other cytokines, directly in the blood have been unsatisfactory.

To date, the study of IL-1 and IL-2 has been concerned primarily with their role in stimulating lymphocyte proliferation and helper and effector function in the adaptive immune response and other forms of host defense. As a result of this focus, study of these cytokines has been limited to stimulation of cells cultured in vitro, or the measurement of blood cytokine levels in vivo in immunological diseases. Recent studies indicate that IL-1 should be considered an "endogenous" component of the circulation; its concentration can vary in a number of "real life" situations.

Generally, in viewing IL-1 and IL-2 or other cytokines as measures of immunocompetence in vivo, investigators have focused on large changes in concentration under severe pathophysiological conditions such as leukemia and arthritis. Furthermore, reports of circulating cytokine levels have been concerned with the elevation in patients compared with controls, while paying little attention to the fact that IL-1 and IL-2 were also detectable in normal subjects and might be subject to modulation by a variety of subclinical factors (Michie, H. R. et al., NEW ENG. J. MED. 318: 1481–1486 (1988); Grau, G. E. et al., LYMPHOKINE RES. 7: 335 (1988); Shenkin, A. et al., LYMPHOKINE RES. 7, 333 (1988)).

In addition to measurement of cytokines in serum or plasma, various cytokines have been detected in other biological fluids. For example, Kimball, E. C. et al., (J. IMMUNOL. 133: 256–260 (1984)) reported IL-1 bioactivity in human urine. Tamatani, T. et al., (IMMUNOLOGY 65: 337–342 (1988)) disclosed the presence of IL-1α and IL-1β in human amniotic fluid, using chromatographic and bioassay methods. The same group used enzyme immunoassays to measure IL-1α and IL-1β in human amniotic fluid (Tsunoda, H. et al., LYMPHOKINE RES. 7: 333 (1988)). Wilmott, R. W. et al., (LYMPHOKINE RES. 7: 334 (1988)) measured IL-1β (by EIA) and IL-1 bioactivity in human bronchoalveolar lavage fluid in cystic fibrosis compared to other diseases. Khan, et al. (MOL. CELL. ENDOCRINOL. 58: 221–230 (1988)) reported that high levels of IL-1-like bioactivity could be demonstrated in human ovarian follicular fluid. Lymphotoxins have been reported in blister fluid of pemphigoid patients (Jeffes, E. W. et al., J. CLIN.

IMMUNOL. 4: 31–35 (1984)). IL-1 has also been reported in human sweat (Didierjean, et al., "Biologically active interleukin 1 in human eccrine sweat: Site dependent variations in α/β ratios and stress-induced increased secretion," CYTOKINE 2: 438–446 (1990)).

IL-1 has been reported to be found in the cerebrospinal fluid (CSF) of cats (Coceani, F. et al., BRAIN RES. 446: 245–250 (1988)) and humans (see, for example, Peter, J. B. et al., NEUROLOGY 41: 121–123 (January 1991)). When Peter et al. (supra) examined IL-1β and tumor necrosis factor (TNF) in CSF and serum of multiple sclerosis patients and normal controls, they concluded that the levels of these cytokines in these two fluids were not of prognostic or diagnostic utility. Westacott, C. I. et al., (ANN. RHEUM. DIS. 49: 676–681 (1990)) used immunoassays to measure cytokines in synovial fluid of patients with rheumatic disease (EIA for IL-1β; RIA for IL-2, TNF, IFN alpha and gamma).

A factor with IL-1-like bioactivity was detected in the gingival fluid of clinically normal humans (Oppenheim, J. J. et al., TRANSPLANT. PROC. 14: 553–555 (1982)), the activity being higher in inflamed than non-inflamed gingival regions. The gingival fluid factor exhibited molecular weights corresponding to both IL- I and epidermal thymocyte-activating factor (Charon, J. A. et al., INFEC. IMMUN. 38: 1190–1195 (1982)). Studies by Jandinski and colleagues using EIA (Jandinski, J. et al., J. DENT. RES. 67: 2307 (1988); Jandinski, J. et al., J. DENT. RES. 68: 526 (1988); Jandinski, J. et al.. J DENT. RES. 68: 1233 (1988)) reported the presence of IL-1α in periodontal tissue, while IL-1 predominated in gingival crevicular fluid of patients with periodontal disease. A more recent study (Kabashimi, H. et al., INFEC. IMMUN. 58: 2621–2627 (1990)) utilizing polyclonal antisera to recombinant human IL-1α and IL-1β and measurement by Western blotting, disclosed that the majority of the IL-1 bioactivity found in gingival crevicular fluid of patients with chronic inflammatory periodontal disease was IL-1, generally considered the membrane-bound form of IL-1. The suggestion was made that the IL-1 was derived by enzymatic cleavage from the cell surface. In this latter study, special care was taken to avoid contamination of the gingival fluid with saliva. These facts argue strongly against a salivary origin for the gingival fluid IL-1.

As can be seen from the foregoing overview of the literature, there have been many attempts to measure endogenous cytokines in blood and other body fluids. However, in reviewing these reports, it is apparent that there is wide variation in the reported results with regard to cytokine concentration in the blood and to fluctuations of cytokine concentration in the blood.

Many reports indicate that cytokines (i.e., IL-2) are not detectable in normal subjects using immunoassays. It is possible that circulating IL-2 may be bound by the well-described soluble IL-2 receptor. The site of attachment may interfere with recognition by the capture antibody of a sandwich assay system, which would make IL-2 appear undetectable. Alternatively, even if the molecule is captured, the detection by the second antibody may be prevented by steric hindrance by the binding of both the capture antibody and the soluble IL-2 receptor to IL-2. In effect, there may not be sufficient space to permit the binding of yet a third large protein. The key element is that the design of these sandwich ELISA assays suggests that they may only pickup a fraction of the total.

It is possible that some assay procedures detect very little cytokine, whereas others pickup none at all. This difference may be related to the assay system or to the cytokine or both. The problem has been reported by the observations of Cannon, J. G., et al., LYMPHOKINE RES., 7: 457–465 (1988), in which the authors show that some plasma substance inhibited the assay, effecting detection. In this study, the authors recommend chloroform extraction of plasma to remove interfering substances. It is not clear from this study if the plasma factors simply effect the performance of the assay or are related to the cytokine itself. This question was further described by Capper, S. J., et al., CYTOKINE 2: 182–189 (1990). Capper, S. J., et al. show that IL-1 α and β are bound by proteins and that the dissociation of these molecules from these serum binding proteins by acidifying the plasma changes the detectable levels. The problem of masking appears to be unique to biological samples collected from in vivo sources; in vitro cell culture supernatants do not contain large quantities of serum binding proteins.

The best example of a cytokine "binding protein" may be inferred from the data describing a soluble IL-2 receptor found in the circulation. This molecule has been shown to be immunologically similar to the low affinity IL-2 receptor on T-cells, "Tac". Its presence in the circulation, free of the T-cell, would strongly argue that it can no longer be a receptor capable of transmitting signals from outside the cell to inside the cell. However, these data do not address the ability of this molecule to still bind IL-2. We would argue that IL-2 in the circulation is bound by this protein, and it is this bound complex which essentially makes the endogenous IL-2 undetectable by "sandwich" assays. Other cytokines (e.g., IL-1) may be bound to other carrier molecules in serum that effectively masks their detection.

In addition, while various cytokines, including IL-1, have been reported in certain normal or pathological biological fluids, there have been no reports of cytokines or lymphokines in saliva or nasal secretions. In fact, a paper reporting a study of the pharmacodynamics of interferon (Diez, R. A. et al., J. INTERFERON RES. 7: 553–557 (October 1987)) stated that ". . . at present, whether interferon is present in saliva and nasal secretion is unclear."

It would be of great benefit if one could easily, accurately and reproducibly measure the concentrations of various endogenous cytokines in the body fluids. This would create a useful window not only into the immune system but into a myriad of physiologically interacting processes. Such tools would be useful in a variety of settings, allowing the collection of data of importance to basic medical sciences, clinical medicine, epidemiology and the forensic sciences.

What is needed is a reliable method of measuring endogenous cytokines in blood which will result in an accurate blood concentration of the cytokine independent of binding proteins which may be bound to the circulating cytokine. In addition, ability to measure cytokines in a biological fluid such as saliva or nasal secretions would simplify the analysis of an individual's immune system, possibly supplanting the need to perform prolonged, tedious and highly variable assays of these cells' behavior in culture.

SUMMARY OF THE INVENTION

The present invention is a competitive solid phase immunoassay for use in detecting and monitoring endogenous cytokines in humans or animals. The competitive solid phase immunoassay is a "one site" immunoassay rather than a "sandwich" assay. The present invention is especially useful for measuring endogenous cytokine levels in the blood and other biological fluids. Prior art methods have been unable to reliably measure cytokine levels in the blood because cytokine-binding proteins (or other blood products) appear to mask the cytokine protein. By measuring the cytokines using the present invention, the concentration of a particular cytokine can be accurately determined. In addition, the present invention is particularly useful in measuring endogenous cytokines in fluids such as saliva, nasal secretions, and tears.

The present invention provides the capability of easily sampling body fluids and thereby measuring "normal" as well as "stimulated" levels of cytokines. The present invention provides a new tool for monitoring these chemical communication signals and their dysregulation in the face of challenges by pathogens, chemicals, therapeutics as well as by biobehavioral factors.

Thus, the present invention is also directed to a method for the non-invasive determination of the level of a cytokine in a human or animal, comprising measuring the concentration of the cytokine in the saliva or nasal secretion of the human or animal utilizing a novel competitive immunoassay. The immunoassay can be an enzyme immunoassay or an immunoassay utilizing other labels such as radioactive elements, luminescent labels, and the like.

The present invention is especially useful in measuring proteins in the blood and other body fluids and includes, but is not limited to, proteins from the group consisting of interleukin-1α, interleukin-1β, interleukin-2, interleukin-6, interferon-alpha, interferon-gamma and tumor necrosis factor-alpha. It is contemplated that the present invention will be useful in detecting and quantifying other cytokine-like molecules in the blood that have not yet been characterized.

In another embodiment, the present invention is directed to a method for monitoring immunological activity of a subject comprising measuring in a non-blood body fluid of the subject the concentration of a cytokine. In a preferred embodiment, the body fluid is saliva. In another embodiment, the body fluid is nasal secretion.

Accordingly, it is an object of the present invention to provide a method for accurately measuring the concentration of endogenous cytokines in body fluids of humans or animals.

It is yet another object of the present invention to provide a method for accurately measuring the concentration of endogenous cytokines in blood of humans or animals.

Another object of the present invention is to provide a method for accurately measuring the concentration of endogenous cytokines in saliva and nasal secretions.

Yet another object of the present invention is to provide a method by which the concentration of cytokines in a body fluid can be correlated to a pathological condition.

Yet another object of the present invention is to provide a method for measuring cytokines.

It is another object of the present invention to provide a method for monitoring cytokine levels which does not require a clinical setting for conducting the tests.

It is yet another object of the present invention to provide a method for evaluating and measuring cytokine levels in response to behavioral perturbations.

It is a further object of the present invention to provide a method for evaluating cytokine levels as a response to chemical, viral or bacterial challenges.

It is yet another object of the present invention to provide a method for monitoring cytokine levels during the course of an identified disease.

It is an object of the present invention to provide a method for using measurements of cytokine levels as an index of the risk of disease.

It is another object of the present invention to provide a method for using cytokine levels as an indicator of clinical flare-ups.

These and other objects, features and advantages of the present invention will become apparent after a review of the following detailed description of the disclosed embodiments and the appended claims.

BRIEF DESCRIPTION OF THE DRAWINGS

FIG. 1 is a graph showing relative antibody titer of rabbit polyclonal antiserum to recombinant human interleukin-1α.

FIG. 2 is a graph showing the immunoreactivity of fractions of an anti-IL-1 antiserum subjected to chromatography.

FIG. 3 is a graph showing an IL-1α standard curve in assay diluent in an EIA.

FIG. 4 is a graph of serum parallelism for the IL-1α-specific EIA. This graph is a logit transformation of the data of FIG. 3 and serum parallelism validation of the IL-1α EIA.

FIG. 5 is a graph showing an IL-2 standard curve in assay diluent (FIG. 4) in an EIA.

FIG. 6 is a graph of serum parallelism, performed as for FIG. 4.

FIG. 7 is a graph showing HPLC validation of fractionated cytokine-spiked serum treated with antibodies specific for IL-1 (FIG. 7A) or IL-2 (FIG. 7B).

FIG. 8 is a Western blot showing a single band of immunoreactive material co-migrating with the 17 kDa WHO standard (lane 1).

FIGS. 9 through 11 are each graphs showing twenty-four hour profiles of IL-1α and IL-2 from three normal female volunteers.

FIG. 12 is a graph showing IL-1α immunoreactivity in saliva. Saliva was diluted 1:5, 1:50 and 1:500 and plotted as the log of the dilution.

FIG. 13 is a graph showing IL-2 immunoreactivity in saliva (dilutions as in FIG. 9).

FIGS. 14 through 20 show the levels of salivary IL-1 and IL-2 in four subjects undergoing physical or psychological stress.

DETAILED DESCRIPTION

Figure 11A:
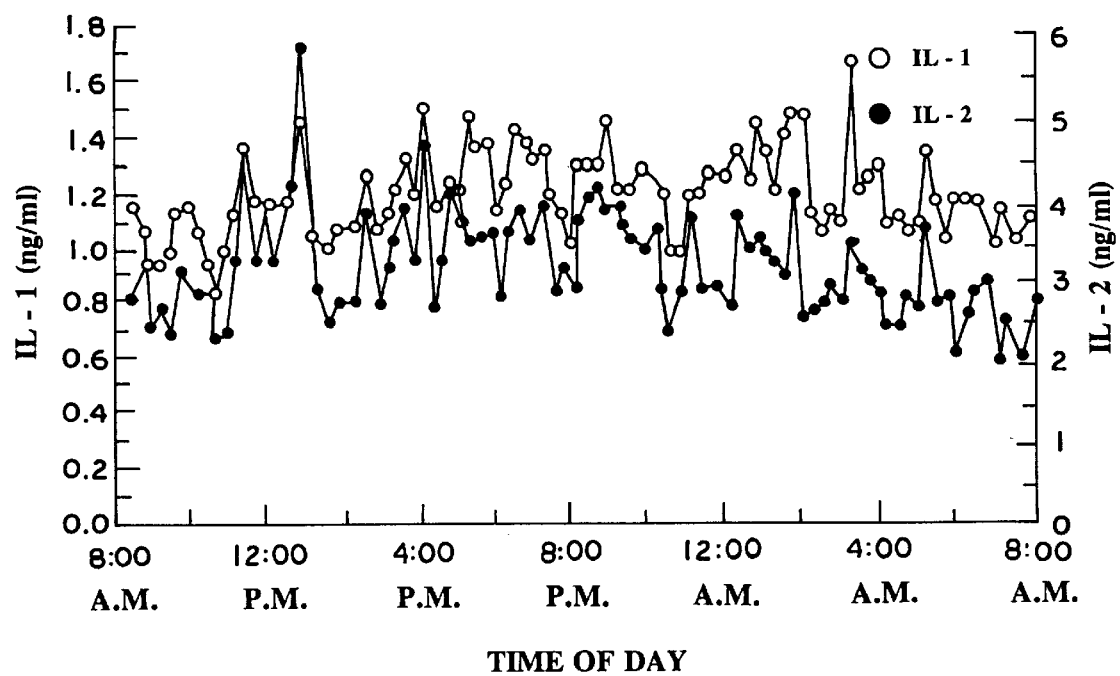

The present invention provides methods for measuring the level of a cytokine in a biological fluid from a human or animal such as blood, saliva, nasal secretions or tears. According to the present invention, cytokine-type proteins can be accurately measured in the blood even in the presence of cytokine binding proteins which mask the cytokine activity in conventional assays.

These methods are particularly useful for monitoring immunological activity in a subject. Such monitoring may be used in (1) subjects undergoing cytokine immunotherapy, or other forms of therapy, (2) patients with immunological disorders in which salivary lymphokine or cytokine levels are abnormal, (3) individuals being studied for the effects of behavioral influences on immune function, and the like. The methods are particularly well-suited for monitoring immunological activity in a non-invasive and non-stressful manner, in individuals responding to various biobehavioral stimuli, such as psychosocial stress.

The methods of the present invention may be used to detect the presence or measure the concentration or level of any of a number of known cytokines or lymphokines, including, but not limited to, IL-1, IL-2, IL-4, IL-6, IFN-alpha, IFN-gamma, TNF- alpha and TNF-beta.

The present inventors have developed competitive EIAs which are capable of being used to accurately measure cytokines in serum as well as saliva and nasal secretions. Being able to measure cytokines in saliva and nasal secretions allows one to measure the proteins in more easily obtainable body fluids than blood.

The present invention includes any one-site assay system that is preferably polyclonal antibody-based. It has been discovered by the present inventors that even though a cytokine may be bound to another molecule in the biological fluid, there is at least be one part of the molecule that is available for site recognition. This site is accessible to polyclonal antibody binding, making it detectable in the one site system.

This hypothesis is further supported by the direct observation of the inventors. In a study in which cell culture supernatants and plasma samples were studied using an IL-2 sandwich assay, it was determined that IL-2 in culture supernatants could be detected, but could not be detected in the plasma samples. These plasma samples were then heated at 57° C. for 30 minutes. The samples were re-analyzed and levels of IL-2 were then detectable. These data suggested that the two-site assay would be problematic, a one-site polyclonal antibody system was developed. This one-site system is capable of detecting IL-2 in normal serum or plasma without further processing. In fact, when the serum is heated as described above, less IL-2 is detected compared to the unheated samples. These observations may be explained by the following: Using the sandwich assay, heating allows one to see something compared to nothing. However, with the competitive assay system the total was already detected.

The methods of the present invention put in the hands of both basic researchers and clinicians a new tool which provides a quick, sensitive and dynamic "snapshot" of the immune system. Using the methods of the present invention, it is possible to obtain a clearer picture of the state of the immune system in a human or animal not only during a major disruption, as in AIDS or autoimmune diseases, but in response to common stressful life events. This information can enlarge the knowledge of the various factors which promote health or disease via effects on the immune system, and will allow individuals, health care providers and society at large to make more rational decisions as to health promoting behaviors.

The method of the present invention for measuring the level of a cytokine in a biological fluid typically comprises incubating the biological fluid in the presence of an antibody capable of binding to the cytokine and detecting the amount of the cytokine bound or not bound to the antibody.

Conventional immunoassays, in particular EIAs, are well known in the art (see, for example, Voller, A., DIAGNOSTIC HORIZONS 2: 1–7, Microbiological Associates Quarterly Publication, Walkersville, Md. (1978); Voller, A. et al., BULL. WHO 53: 55–65 (1976); Voller, A. et al., J. CLIN. PATHOL. 31: 507–520 (1978); Butler, J. E., METH. ENZYMOL. 73: 482–523 (1981); Maggio, E. (ed.), ENZYME IMMUNOASSAY, CRC Press, Boca Raton, Fla. (1980); Hevey et al., U.S. Pat. No. 4,228,237; Parikh et al., U.S. Pat. No. 4,298,685, which references are hereby incorporated by reference).

The present inventors have developed a novel competitive form of the enzyme linked immunosorbent assay (ELISA) (see also Plebani et al., J. IMMUNOL. METH. 90: 241 (1986)) to measure hormones and growth factors in biological matrices. The manner by which an unknown ligand, such as a cytokine, is detected is similar to that of a competitive radioimmunoassay. Briefly, a specific amount of a labeled analyte, for example, labeled biotinylated IL-1, is in competition with unlabeled IL-1 (either in the unknown sample or in a standard) for a limited number of antibody binding sites.

The above method is preferably an immunoassay, more preferably, an enzyme immunoassay, most preferably, a competitive enzyme immunoassay. The above method provides a method for monitoring immunological activity of the subject wherein the measurement is performed on more than one occasion. Furthermore, the above method provides a method for monitoring cytokine therapy in a subject wherein the subject being monitored is one undergoing cytokine therapy. Preferably, the cytokine being monitored is the cytokine of the immunotherapy.

In a preferred embodiment of the present invention, in the first step of the assay, an antibody, preferably a rabbit polyclonal antibody which recognizes many epitopes on the cytokine molecule, is adsorbed to a solid phase support or carrier, preferably the wells of a polystyrene EIA plate. This antibody, known as a "capture antibody," is then used to bind the labeled analyte, e.g. biotinylated IL-1, and the unlabeled analyte in the sample or the standard. After appropriate washing steps, an enzyme-conjugated binding partner for the label, for example, streptavidin or an anti-biotin antibody, is incubated with the antibody-analyte complex, allowing the enzyme to be bound to the complex. After removal of any unbound enzyme-conjugated binding partner, a chromogenic enzyme substrate is added. The bound enzyme converts the substrate to a colored product which can be detected by colorimetric means. The amount of color that develops per unit time is inversely proportional to the amount of analyte present in the sample. As the concentration of analyte, for example IL-1, increases, the amount of color generated decreases. This is because the larger amount of IL-1 in the sample competed successfully with the fixed amount of biotinylated IL-1 for binding to a fixed amount of immobilized antibody, and bound non-labeled IL-1 does not result in subsequent binding of the binding partner-enzyme complex.

The competitive EIA according to the present invention is designed to be performed rapidly, preferably within seven hours, although it has the flexibility of being used as an overnight assay. In a preferred form of the assay, during the first two hours, the capture antibody, preferably a rabbit anti-human cytokine antibody, is adsorbed to the wells of a 96-well immunoplate. During the next two hours, unbound antibody is washed off the plate followed by addition of either standards or unknowns, as well as a specific amount of labeled cytokine, preferably biotinylated cytokine. The amount of labeled cytokine which has bound is then detected by the addition of the binding partner, preferably streptavidin, conjugated to an enzyme, preferably alkaline phosphatase, followed by addition of the chromogenic substrate, preferably p-nitrophenyl phosphate. The resultant color is then read as absorbence (or optical density, O.D.) at an appropriate wavelength, e.g., 405 nm for p-nitrophenyl phosphate disodium. The color can be read using a colorimeter, such as an ELISA plate reader, at several time points, for example 4 and 24 hours.

The term "solid phase support" means any support capable of binding antigen or antibodies. Well-known S supports, or carriers, include, but are not limited to, polystyrene, polypropylene, polyethylene, glass, dextran, nylon, amylases, natural and modified celluloses, polyacrylamides, aaaroses, and magnetite. The support material may have virtually any structural configuration so long as the antigen is capable of binding to an antibody. Thus, the support configuration may be spherical, as in a bead, or cylindrical, as in the inside surface of a test tube, or the external surface of a rod. Alternatively, the surface may be flat such as a sheet, test strip, etc. A preferred carrier is the bottom and sides of a polystyrene microtiter plate well. Those skilled in the art will know many other suitable carriers for binding antibody or antigen, or will be able to ascertain the same by use of routine experimentation.

A preferred means of labeling the analyte, e.g., the cytokine (or anti-cytokine antibody, as discussed below) is by linking to it to label which can be bound to a binding partner which is conjugated to an enzyme in an EIA. This enzyme, in turn, when later exposed to its substrate, will react with the substrate in such a manner as to produce a chemical moiety which can be detected, by spectrophotometric, fluorometric or by visual means. Enzymes which are useful in the EIA method of the present invention include, but are not limited to, alkaline phosphatase, glucose oxidase, $\beta$-galactosidase, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, asparaginase, ribonuclease, urease, catalase, glucose-6-phosphate dehydrogenase, glucoamylase and acetylcholinesterase.

It is also possible to label the analyte (or antibody) with a fluorescent compound. When the fluorescent labeled bound analyte is exposed to light of the proper wave length, its presence can then be detected due to fluorescence. Among the s most commonly used fluorescent labeling compounds are fluorescein isothiocyanate, rhodamine, phycoerythrin, phycocyanin, allophycocyanin, o-phthaldehyde and fluorescamine.

The analyte or antibody can also be labeled with fluorescence emitting metals such as $^{152}$Eu, or others of the lanthanide series. These metals can be attached to the analyte or antibody using such metal chelating groups as diethylene-triaminepentaacetic acid (DTPA) or ethylenediaminetetraacetic acid (EDTA).

The analyte or antibody also can be labeled by coupling it to a chemiluminescent compound. The presence of the chemiluminescent-tagged bound molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the analyte or antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In addition to use of the enzyme immunoassay, the method of the present invention can measure the level of a cytokine using any of a variety of other immunoassays. For example, by radioactively labeling the cytokine (or the cytokine-specific antibodies or antibody fragments as described below), it is possible to detect the cytokine through the use of a radioimmunoassay (RIA). A good description of RIA may be found in Weintraub, B., PRINCIPLES OF RADIOIMMUNOASSAYS, Seventh Training Course on Radioligand Assay Techniques, The Endocrine Society, pp. 1–5, 46–49 and 68–78 (March, 1986). See also: Work, T. S. et al., LABORATORY TECHNIQUES AND BIOCHEMISTRY IN MOLECULAR BIOLOGY, North Holland Publishing Company, New York (1978).

The radioactive isotope can be detected by such means as the use of a gamma counter or a scintillation counter or by autoradiography. Isotopes which are particularly useful for the purpose of the present invention are $^3$H, $^{125}$I, $^{131}$I $^{35}$S $^{14}$C and preferably $^{125}$I.

The binding activity of a given lot of anti-cytokine antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

Detection of the labeled antibody or binding partner for the labeled analyte may be accomplished by a scintillation counter, for example, if the detectable label is a radioactive gamma emitter, or by a fluorometer, for example, if the label is a fluorescent material. In the case of an enzyme label and a chromogenic substrate, the detection can be accomplished by calorimetric methods. Detection may also be accomplished by visual comparison of the extent of enzymatic reaction of a substrate in comparison with similarly prepared standards.

In one embodiment of the present invention, a body fluid such as saliva or nasal secretions are collected in a tube. For, example, a subject is asked to expectorate or allow his saliva to flow into an appropriately placed collecting container. Stimulants of salivary secretion, such as a stick of chewing gum or crystalline stimulant, such as citric drink mix or tart candy, may be used to enhance the flow of saliva.

In another embodiment, a more sophisticated collection procedure entails the extraction of clarified saliva from dental cotton. A preferred embodiment is to coat the dental cotton with a sugar-free, powdered drink mix, which then serves as both stimulant for salivary secretion and as a "sink" for saliva collection. Clarified saliva is then extracted by placing the saturated cotton into the barrel of a 5 cc disposable plastic syringe. The plunger is reinserted into the barrel and a collection tube is placed at the tip of the syringe. The dental cotton is then compressed, forcing the clarified saliva out of the cotton.

In another embodiment, a more sophisticated collection device may be used, for example, an oral-diffusion sink (Wade, S. E., U.S. Pat. No. 4,594,326; U.S. Pat. No. 4,798,207, which references are hereby incorporated by reference in their entirety). Such a device allows the measurement in a time-integrated fashion of the concentration of substances in a fluid, preferably saliva. The device is installed in the mouth of a subject where it accumulates compounds of interest, preferably a cytokine as described herein, by passive diffusion. The device is a small, sealed plastic cylinder with a plurality of tiny ports covered by a selectively permeable membrane such as a dialysis membrane. These ports define a limited pathway for diffusion of the substance being measured, said substance accumulating in the device in relation to its concentration gradient. A gradient may be maintained by providing within the inner chamber of the device a substance which can bind the substance to be measured, for example an antibody specific for the cytokine. More recently, the utility of such a device for the time-integrated measurements of corticosteroids in human saliva has been demonstrated (Wade, S. E. et al., CLIN. CHEM. 37: 1166–1172 (1991)). These studies demonstrate that the rate of uptake of the hormone by the device is (a) independent of the mass-flow properties of the medium in which it is used, (b) the performance of the device is unaffected by substantial blood contamination of saliva, (c) the device can accurately integrate even extreme episodic changes in hormone concentration; and (d) individual differences in saliva from human subjects are easily demonstrable.

The present invention also provides test kits for use with the methods of the present invention. The kit of the present invention is useful for measuring cytokines in a body fluid, preferably saliva or nasal secretions. Each kit contains detailed instructions on the collection of the biological fluid, e.g., saliva, the assay method and interpretation of results. The kit is preferably assembled under Quality Assurance procedures applicable to in vitro diagnostic products licensed as medical devices by the Food and Drug Administration.

In a preferred embodiment, the kit comprises:
(a) a container means for collecting said saliva or nasal secretion;
(b) a second container containing a first binding partner specific for the cytokine to be measured;
(c) a third container containing purified cytokine in labeled form; and
(d) a fourth container containing a second binding partner for said label on said labeled cytokine. The above kit preferably further comprises:
(e) a solid phase carrier.

In a preferred format, a kit contains enough reagents to perform analysis of 80 unknowns (in duplicate).

Preferably the kit contains a device for collection of the biological fluid, such as a sampling tube for saliva, a passive oral diffusion sink as described above or an equivalent thereof, or an aspirator for obtaining a nasal secretion. Optionally, the kit may contain a substance for stimulating the production or flow of the bodily fluid, such as chewing gum for stimulating salivary flow, methacholine for stimulating nasal secretions, and the like.

In a preferred embodiment, the kit of the present invention comprises:
(1) a capture antibody specific for the cytokine to be measured;
(2) purified cytokine in labeled form;
(3) standard human cytokine to serve as the assay standard; and
(4) enzyme conjugated binding partner for the label on the labeled cytokine. The kit may optionally contain:
(5) chromogenic substrate for the enzyme;
(6) coating buffer comprising 15.9 g/l $Na_2CO_3$, 29.3 g/l $NaHCO_3$, and 0.1 to 1 µg/ml gelatin;
(7) standard diluent;
(8) substrate buffer;
(9) wash buffer; and
(10) two 96-well polystyrene EIA plates.

In a preferred embodiment, for measuring IL-1α, the kit of the present invention contains:
(1) purified polyclonal rabbit anti-human IL-1α antibody (the capture antibody);
(2) biotin-conjugated human recombinant IL human recombinant IL-1α; and
(3) Streptavidin conjugated to alkaline phosphatase.

In a preferred embodiment, the kit as described above additionally contains:
(4) p-nitrophenyl phosphate disodium (substrate);
(5) coating buffer, comprising 15.9 g/l $Na_2CO_3$, 29.3 g/l $NaHCO_3$, and 40 mg/l BSA;
(6) standard diluent, comprising phosphate buffered saline, pH 7.4, supplemented with 0.1% BSA and 0.1 % $NaN_3$;
(7) substrate buffer, comprising 1.255 g/l $Na_2CO_3$, 0.844 g/l $NaHCO_3$, and 0.203 g/l $MgCl_2$;
(8) wash buffer, comprising PBS supplemented with 0.2% Tween-20 and 0.1% $NaN_3$;
(9) two 96-well polystyrene ELISA plates.

Such a kit may comprise a carrier being compartmentalized to receive in close confinement therewith one or more containers such as vials, tubes, and the like, each of said containers comprising the separate elements of the immunoassay.

For example, there may be a container containing the capture antibody in fluid phase or alternatively, already immobilized on a solid phase support. A further container contains labeled (e.g., biotin- or enzyme-conjugated) cytokine, or labeled antibodies in solution. Further containers may contain standards comprising serial dilutions of the cytokine to be detected. The standard solutions of the cytokine are used to prepare a standard curve with the concentration of the cytokine plotted on the abscissa and the detection signal on the ordinate. The results obtained from a sample, e.g. saliva, containing the cytokine may be interpolated from such a plot to give the concentration of the cytokine.

In the above kit, the cytokine is preferably selected from the group consisting of interleukin-1α, interleukin-1β, interleukin-2, interleukin-6, interferon-alpha, interferon-gamma and tumor necrosis factor-alpha. Most preferably, the cytokine is interleukin 1α, interleukin-1β, or interleukin-2.

In one embodiment of the above kit, a preferred label for the cytokine is biotin and a preferred second binding partner is streptavidin. In a preferred embodiment, the first binding partner is a capture antibody specific for the cytokine, the second binding partner is an enzyme-conjugated binding partner, preferably enzyme conjugated-streptavidin. Preferably, the enzyme is alkaline phosphatase. The kit may additionally comprise a chromogenic substrate for the enzyme.

The kit of the present invention preferably contains detailed instructions on the collection of the biological fluid, e.g., saliva, the assay method and the interpretation of results. The types of assays which can be incorporated in kit form are many, and include, for example, competitive and noncompetitive assays, including RIA, EIA, ELISA, and immunometric, or sandwich, immunoassays.

The methods of the present invention eliminate the risk and stress associated with sample collection by phlebotomy. The assay methods of the present invention provide a useful monitoring tool to facilitate research in human or animal subjects, both normal and diseased. The methods of the present invention, for the first time, place simple, noninvasive, reliable, reproducible and objective analytical instruments into the hands of those wishing to study the immune system of humans, such as researchers interested in brain-immune system interactions or physicians following a patient being treated with cytokines, agents that affect cytokine levels or agents that act upon the immune system and whose action may be reflected as altered cytokine concentrations in a body fluid, such as saliva.

Having now generally described the invention, the same will be more readily understood through reference to the following examples which are provided by way of illustration, and are not intended to be limiting of the present invention, unless specified.

EXAMPLE I
Generation and Purification of Polyclonal Antibodies Specific for Interleukin-1α and Interleukin-2

Pathogen-free New Zealand white rabbits, S weighing approximately 2–3 kg, are quarantined and acclimated in a pathogen-free facility for 2 weeks prior to obtaining a preimmunization blood sample from each animal. One week after the pre-immunization bleed, a 1:1 dilution of an immunogenic enhancer comprising colloidal gold having an alkaline pH, mixed at a ratio of 2:1, antigen solution to gold (Assay Research, Inc.) is mixed with 500 μg of each peptide. The enhancer allows the peptide to act as the immunogenic molecule without prior conjugation to other larger and more antigenic molecules such as BSA or KLH. For the first immunization, the peptide-adjuvant mixture is emulsified in Freund's complete adjuvant and injected subcutaneously into one rabbit. Two weeks later the peptide/enhancer mixture is emulsified in Freund's incomplete adjuvant and is injected subcutaneously. Three days after this injection, five ml of blood is drawn through an ear vein and the resultant sera is tested for antibody titers (described below). Approximately two weeks after the second injection, each rabbit is boosted with only the peptide/enhancer mixture and bled four days later. Subsequent injections, containing only the peptidelenhancer mixture, and bleeds are performed once a month.

Titration and Purification of IL-1 and IL-2 Antisera

After a second injection of either IL-1 or IL-2 into a rabbits, a five ml blood sample is drawn and the serum tested for antibody titer. FIG. 1a demonstrates that the immunogenic enhancer facilitated the generation of very high titer antiserum specific for IL-1α. As shown, a two log dilution of the neat sera (i.e., 1:100 dilution to 1:10,000 dilution) does not decrease the signal generated. A similar titer is observed for the antiserum specific for IL-2. Although the antisera titers are high, the neat sera can not be used for further assay development due to the unacceptable background color generation. Consequently, both antisera are purified as described below.

Each polyclonal antiserum is purified by column chromatography using a mixed ion exchange resin (J. T. Baker, Inc., Phillipsburg, N.J.). The resin-bound antibody is eluted from the column using a linear gradient of 0 to 0.75 M NaCl in 25 mM MES (2-[N-Morpholino]ethanesulfonic acid) (pH 5.6 with no NaCl, pH 7.0 at 0.75 M NaCl). Five ml fractions are collected and analyzed for protein content (absorption at 280 nm). The presence of specific antibodies is tested by a direct enzyme immunoassay (EIA). Rabbit antibodies are detected by an alkaline phosphatase-conjugated goat anti-rabbit antibody. Those fractions which result in a signal-to-noise ratio of five or more are pooled and dialyzed against PBS. The resultant pooled aliquots serve as the antibody solution for their respective EIAs.

Depicted in FIG. 2 is a typical chromatogram observed from the mixed ion exchange purification of the IL-1α antiserum. The resin fractionates the serum into two major fractions: one fraction containing serum contaminants such as albumin and transferrin (fractions 1–10; closed circles) and the other fraction containing a highly enriched immunoglobulin fraction (fractions 12–30; open circles). After testing, only those fractions which give a signal to noise ratio of 5 or better are pooled and dialyzed against PBS (FIG. 2; open circles).

EXAMPLE II
Direct and Competitive Enzyme Immunoassays

1. Titration of Antisera

The test bleeds for either peptide and all subsequent production bleeds are tested for relative antibody titers by a direct EIA. Either IL-1 or IL-2 is diluted in coating buffer (15.9 g/L $Na_2CO_3$, 29.3 g/l $NaHCO_3$, pH 9.6) to a concentration of 10 μg/ml. One hundred μl of this solution is dispensed into 16 wells of a 96-well microtiter plate and incubated for 2 hours at room temperature. During this incubation, serum samples from both the pre-immunization bleed and test bleed for each peptide are diluted 1:100, 1:1,000 1:10,000 and 1:100,100 in assay diluent (phosphate buffer saline (PBS) containing 0.1% $NaN_3$).

After the incubation, the wells are washed with 300 μl of wash buffer (0.2% Tween-20 solution in PBS), and 100 μl of the diluted sera are added to designated wells and incubated for one hour. Following this incubation, the wells are washed with wash buffer, followed by addition of 100 μl of alkaline phosphatase-conjugated goat anti-rabbit antisera to each well. This mixture is incubated for one hour followed by washing. The chromogenic substrate, p-nitrophenyl phosphate disodium (Sigma Chemical Co., St. Louis, Mo.) and the color reaction (absorption at 405 nm; A405) is measured within 15 minutes with an ELISA plate reader.

2. Measurement of IL-1 and IL-2

Purified antiserum against either IL-1 or IL-2 is diluted 1:10,000 in coating buffer, and 100 μl are added to wells of a microplate and incubated for 2 hours. The wells are then washed with wash buffer and standards or unknown samples are added in a volume of 50 μl and incubated for 1 hour. A standard curve is generated using 6 concentrations of IL-1 or IL-2 (100, 25, 6.25, 1.563, 0.39 and 0.098 ng/ml). To account for possible matrix effects, the standards were diluted in assay diluent or in a 50% serum solution from which endogenous IL-1 or IL-2 has been pre-absorbed (discussed below). Following the 1 hour incubation, 50 μl of conjugated IL-1 or IL-2 (Assay Research, Inc.) is added to the wells and allowed to compete with IL-1 or IL-2 in the standards or samples for an additional 1 hour. The wells are then washed and incubated for 45 minutes with alkaline phosphatase conjugated anti-rabbit antibody (Assay Research, Inc.) followed by the addition of substrate. The resultant color reaction is determined at an absorbance of 405 nm. The data for the standard curve, as well as the potency estimates for the unknowns are analyzed by computer-assisted four parameter log-logit curve software (Microplate Manager, Bio-Rad, Richmond, Calif.).

FIGS. 3 through 6 demonstrate classical competition kinetics in EIAs for both the IL-1 (FIGS. 3 and 4) and IL-2 (FIGS. 5 and 6). A sigmoid curve is generated when plotting the log of the cytokine standard concentration against the resulting absorbence at 405 nm (OD405) (FIGS. 3 and 5). When the observed absorbence values are converted to a logit function, a straight line is generated (FIGS. 4 and 6). The limit of detection of both assays is 98 pg/ml corresponding to a mole value of $2.8 \times 10^{-16}$ moles of IL-1/well and $3.6 \times 10^{-16}$ moles of IL-2/well, with a linear range of 0.4 to 25 ng/ml. Furthermore, the $ED_{50}$ (concentration at which 50% competition occurs) for both assays is about 1.0 to 1.5 ng/ml.

When serum is added to the reaction, significantly less color is generated. This indicated that less binding occurred, thereby invalidating the measurement of unknown samples in 100% serum. However, upon examining the effects of serial dilution of the serum, a 50% mixture of serum and assay diluent give results which are comparable to both threshold of detection and $ED_{50}$ to the standard curve generated in assay diluent alone. A maximum of 50% serum or plasma can be used without adversely affecting the standard curve.

EXAMPLE III

Validation of Assays

1. Effects of Serum

Both the IL-1 and IL-2 EIAs are validated by performing parallel studies of standards in serum vs. standards in PBS, and by quantitative recovery of added cytokines in serum. Serum parallel experiments are performed by serial dilution of the serum samples which contained immunoreactive IL-1 and L-2 with assay diluent and are used as unknowns in both the IL-1 and IL-2 EIAs. Upon development of the EIAs, the absorbence values for both the standard curve and serially diluted serum samples are analyzed for parallelism.

The effect of serum on the performance of the IL-1 and IL-2 EIAs require testing, because one of the primary objectives for the assays is to determine if IL-1 and IL-2 occurred endogenously in the circulation. This is accomplished by two separate methods. The first study examined is quantitative recovery of the cytokines from serum to which known amounts of the cytokines has been added ("cytokine-spiked serum"). For this assay, standard curves are generated in either standard diluent or human serum diluted 1:1 with assay diluent.

Parallel studies demonstrated that the standard curves generated in either assay diluent or 50% human serum are parallel (FIGS. 4 and 6). Thus, serum-containing samples, although exhibiting a matrix effect, do not contain nonspecific factors which inhibit the binding of IL-1 or IL-2 to their respective antibodies. Furthermore, the slope and the $ED_{50}$ value for both assays (either done in assay diluent or in pre-absorbed serum) are very similar, indicating that serum from which immunoreactive IL-1 or IL-2 is removed can be used as a carrier matrix for the determination of endogenous IL-1 and IL-2 levels.

2. Absorption Analysis

The second approach involves absorption of a cytokine by its respective antibody and analysis of the absorbed material by high performance liquid chromatography (HPLC). For this study the antibodies are diluted 1:500 in coating buffer, and 100 μl of either antibody is added to the EIA plate. Twenty-four hours later, the plates are washed with wash buffer and 100 μl of serum containing either IL-1 or IL-2 is added to the appropriate wells and incubated overnight. After the incubation, the plates are washed with wash buffer and the well-bound material is eluted from the well by the addition of 100 μl of 2M NaCl followed by quick-freezing the plate at –80° C. The eluted material is separated on a gel filtration HPLC sizing column which has been equilibrated with 100 μg/ml BSA in 100 mM $NaHPO_4$ buffer. Fractions of 1.5 ml are collected every minute and quickly frozen. The immunoreactivity of each fraction is then compared to the immunoreactivity of HPLC-fractionated standard.

One minute fractions, collected from a linear HPLC gradient separation of the cytokine diluted in assay diluent, are tested in their respective EIAs. The resultant immunoactivity is then compared to the immunoreactivity of serum which has been fractionated by HPLC, captured by antibody and spiked with the cytokine (FIG. 7). IL-1 or IL-2 antibodies used in the EIAs are used to capture the IL-1 or IL-2 from the cytokine-spiked serum. The results indicate that the material captured on the plate migrated to the same position in the chromatogram as the standard. FIG. 7 demonstrates that the immunoreactivity of antibody-absorbed serum is highest in those fractions which co-eluted with the authentic IL-1 or IL-2 standard, although other proteins are detected based on absorbence at 280 nm.

3. Western Analysis

The IL-1 antibody-captured sample was also tested by Western blot analysis. FIG. 8 indicates that a single band of immunoreactive material co-migrates with the 17 kDa WHO standard, although Coomassie blue staining of the SDS-PAGE gel indicates the presence of many additional proteins.

4. Cross Validation with IL-2 Bioassay

The IL-2 EIA is cross-validated against an IL-2 bioassay, using a recombinant IL-2 standard diluted in serum. The bioassay consists of measuring the proliferative response of the IL-2 dependent cell line, CTLL-2, as a function of the amount of lactic acid in the culture well, caused by various concentrations of IL-2 either in the standard or other reference standard. This response is compared with the potency estimate of that standard as calculated from the IL-2 EIA standard curve. Finally, a cross absorption study is performed to determine if serum, containing IL-1 and IL-2 immunoreactivity, shows diminished IL-1 or IL-2 levels following immunoabsorption with either the IL-1 or IL-2 antibodies. Prior to the experiment, the sample is shown to contain 2.5 ng/ml IL-1 and 20 ng/ml IL-2. The sample is divided into two aliquots and incubated with either IL-1 or IL-2 antibody under standard assay conditions. Subsequently, the sample is removed from the wells and analyzed for IL-1 and IL-2 levels in a later assay.

Internal standards, routinely measuring 4 and 15 U/ml in the bioassay, are calculated to contain 3.1 and 17.5 U/ml, respectively, in the EIA. Each EIA is tested for cross-reactivity with other cytokines or serum factors.

5. Analysis of Cross-Reactivity

In each assay, cross-reactivity of the reagents with other cytokines and major serum factors is also tested. In this study, each cytokine is tested at the highest concentration of standard (100 ng/ml) in each EIA, while the serum factors are tested at concentrations of up to 1 mg/ml. The results are presented as % cross-reactivity of each cytokine as calculated by the following equation:

$$\% \text{ Cross-reactivity} = \frac{\text{Conc. of Nonspecific Reagent} \times 100}{\text{Actual Concentration}}$$

Both the IL-1 and IL-2 EIA demonstrate a very high degree of specificity. Neither assay recognizes any of the other cytokines tested to any significant extent, the cross-reactivity ranging from 0 to 0.5% (Table 1). Furthermore, the serum factors tested do not interfere with the assay at concentrations that exceeded the standard concentration by 100,000-fold. The cross-absorption study demonstrated that the IL-1 and IL-2 antibodies specifically recognize their respective cytokine in serum. For example, IL-1 levels do not change when the serum sample is treated with the IL-2 antibody.

Following absorption of the sample with the anti-IL-2 antibody, IL-1 levels decrease from 3 to 2.5 ng/ml.

In contrast, when the sample is absorbed with the anti-IL-1 antibody, the IL-1 concentration falls to 1.5 ng/ml. Similarly, absorption with the anti-IL-2 antibody decreases measured IL-2 levels from 18 ng/ml to 2 ng/ml, whereas absorption with the anti-IL-1 antibody has essentially no effect (IL-2 concentration of 16 ng/ml).

TABLE 1

Cross-Reactivity (in %) of Cytokines and Other Serum Components with IL-1α and IL-2 EIAs

| Test Substance | IL-1α EIA | IL-2 EIA |
|---|---|---|
| IL-1α | 100 | 0.0 |
| IL-1β | 0.1 | 0.0 |
| IL-2 | 0.1 | 100 |
| IL-3 | 0.0 | 0.0 |
| IL-4 | 0.0 | 0.0 |
| IL-6 | 0.0 | 0.5 |
| TNFa | 0.0 | 0.0 |
| GM-CSF | 0.0 | 0.0 |
| G-CSF | 0.0 | 0.0 |
| M-CSF | 0.0 | 0.0 |
| IgG | 0.0 | 0.0 |
| Hemoglobin β | 0.0 | 0.0 |
| Bilirubin | 0.0 | 0.0 |
| a2-macroglobulin | 0.0 | 0.0 |

Abbreviations:
TNF-tumor necrosis factor;
GM-CSF: granulocyte/macrophage colony stimulating factor;
G-CSF: granulocyte colony stimulating factor;
M-CSF: macrophage colony stimulating factor.

EXAMPLE IV
Measurement of 24 Hour Profiles of IL-1 and IL-2 in Humans

Three normal female volunteers are recruited through the Normal Volunteer Program, National Institutes of Health as part of an ongoing study of 24-hour neuroendocrine profiles being conducted by the Neuroendocrinology Branch, National Institutes of Mental Health. Blood samples are drawn through an indwelling heparin lock every 15 minutes for 24 hours. Samples are collected and placed on ice and batch centrifuged every 6 hours. The resultant plasma is harvested and stored at −70° C. until thawed for analysis. Samples are run as duplicates in each assay and are analyzed for both IL-1α and IL-2 at the same time. Peak frequency and duration is determined by the Cluster Analysis (Veldhuis, J. D. et al., AM. J. PHYSIOL. 250:E48693 (1986)).

Figure 11B:
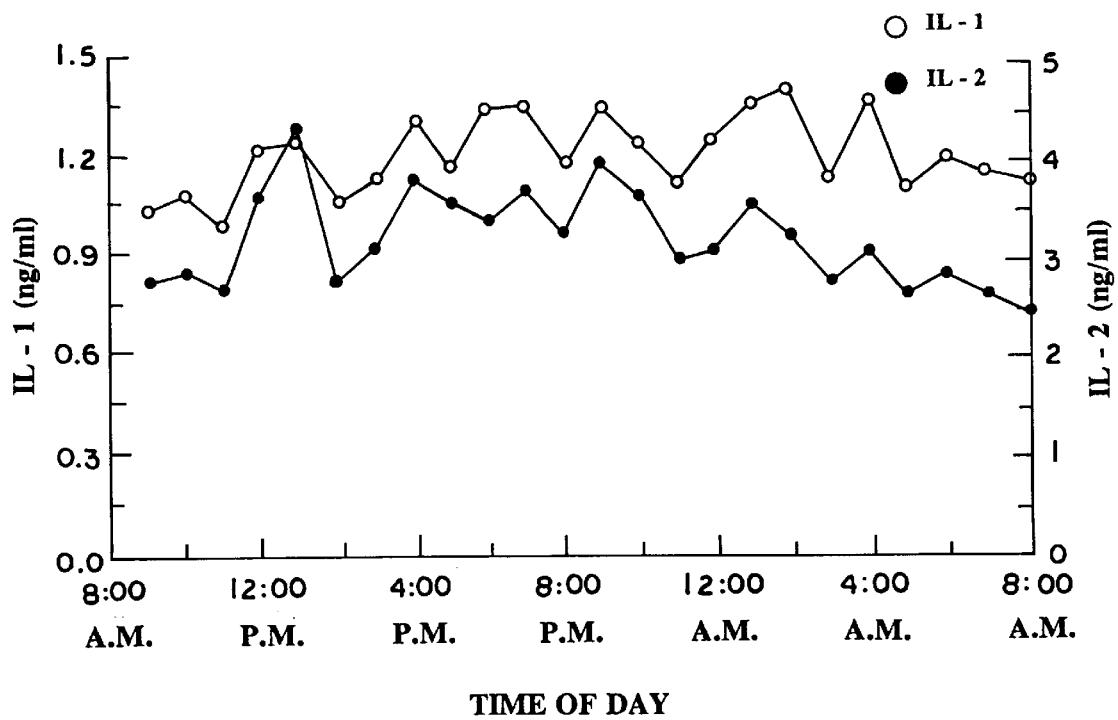
Figure 20:
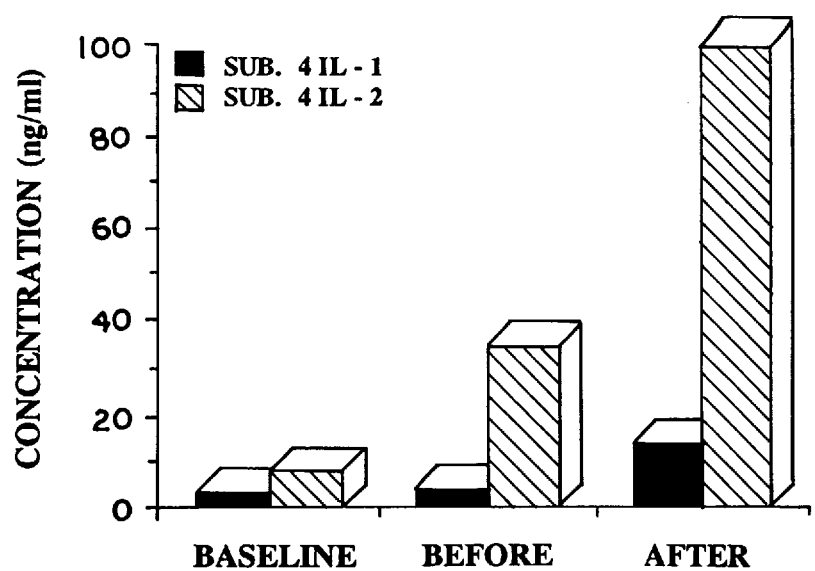

Data from these three normal volunteers indicated that IL-1 and IL-2 levels are not stable throughout the day, with a large number of cytokine spikes occurring throughout the day (FIGS. 9–11). The data demonstrate that changes in IL-1 levels are temporally reflected by changes in IL-2 levels, with IL-2 levels consistently higher at each time point. This conclusion is further supported by computer-assisted pulse frequency analysis in which temporal peaks and their durations are identified. This analysis indicates that virtually all IL-1 peaks and their durations are matched by temporally coincident increases in L-2. As previously demonstrated this temporal coincidence is not related to assay cross-reactivity because neither assay detects the alternate cytokine.

To determine if an underlying 24-hour rhythmic secretory profile exists, mean hourly levels are calculated from the quarter-hourly data for each individual (FIG. 8, lower panels). From the limited number of subjects examined, it is difficult to determine if any consistent secretory profile is present.

Thus, the cytokine levels measured in human serum by the EIA according to the present invention range from 0.5–1.5 ng/ml for IL-1 and 1 to 8 ng/ml for IL-2. It is interesting to note that the cytokine levels reported herein are an order of magnitude lower than the reported dissociation constants of their respective receptors (Kilian, P. L. et al., J. IMMUNOL. 136: 4509–4514 (1986); Dower, S. K. et al., J. EXP. MED. 162: 501–515 (1985)). This relationship between receptor affinity and circulating hormone concentration is consistent with other well described endocrine systems.

The results reported herein demonstrate that IL-2 levels appear to mirror, and be an amplification of, the IL-1 signal. Because IL-1 stimulates IL-2 production and secretion (Smith, K. A., supra), the temporal coincidence of the two patterns and the finding of higher levels of IL-2 than IL-1 are consistent with the well described IL-1/IL-2 cascade within the immune system.

EXAMPLE V
Measurement of Cytokines in Saliva

Saliva is collected using a method described by Kahn, J. P. et al., BIOL. PSYCHIAT. 23: 335–349 (1988). Subjects chew half a stick of sugarless gum 3 times without swallowing their saliva. Saliva is collected in 15 ml conical test tubes by placing the tube to the mouth and allowing the saliva to flow into the tube. Subjects are instructed not to try to spit into the tube but rather to allow accumulated saliva to come to their lips and flow into the tube. Average collection is approximately 2 to 3 ml. Alternatively, saliva can be collected by coating a dental cotton with a sugar-free tart drink mix such as lemonade flavored Crystal Light™. The coated-cotton is placed between the gum and cheek for 2 to 3 minutes. The cotton is removed and placed in the barrel of a 5 cc syringe. The plunger to the syringe is replaced and a test tube is placed at the outlet of the syringe. The cotton is squeezed with the plunger and the saliva that is in the cotton is collected in the test tube. The collected solution is clarified saliva and is ready for analysis.

The results of EIA determination of salivary IL-1α and IL-2 levels are shown in FIG. 12 and 13, respectively. In this study saliva from two subjects was serially diluted with Standard Diluent. The resultant OD's from the dilution were compared to the Standard dilution curve. The data show that serial dilution of saliva results in a curve that parallels the serial dilution of the Standards.

EXAMPLE VI
Measurement of Cytokines in Nasal Secretions

As with saliva, a band corresponding to a molecular weight of about 60–30 kDa is observed in a Western blot of nasal secretions developed with an anti-IL-2 antibody. Pretreatment of the starting material with the anti-IL-2 antibody absorbed out this band. However, if the sample is overloaded with IL-2 antigen prior to the absorption step, the band is no longer absorbed. These results indicate that a higher molecular weight form of IL-2 immunoreactive material is present in nasal secretions.

EXAMPLE VII
Physical and Psychological Stress Modulates Salivary Cytokines

The levels of salivary IL-1 and IL-2 are measured in 14 and 15 year old males during a period of science midterm examinations. For measurements of the psychological stressor, the exam, saliva samples are obtained five days after the exam for determination of background levels. On exam days, saliva samples are obtained within ten minutes before the exam ("Before") and five minutes after the exam ("After"). The effects of a physical stressor, running up and down a staircase five times, is also evaluated at least seven days after the above exams. Prior to exercise, a sample is obtained for background level. After three runs up and down the stairs, a second saliva sample is obtained. Finally, upon completion of the exercise session, another sample is obtained. These data are compared to a sample taken 2 weeks after the mental and physical trials ("baseline"). The results are shown in FIGS. 14–20 and indicate that physical exercise is accompanied by significant rises in IL-1 and IL-2 concentrations. Psychological stress appears to have a greater anticipatory effect, wherein cytokine levels increase prior, and in anticipation of, the school examination.

EXAMPLE VIII
Use of Salivary Cytokine Levels to Predict Clinical Symptoms

A number of autoimmune diseases (Theofilopoulos, A., In: D. P. Stites, et al., eds., BASIC AND CLINICAL IMMUNOLOGY, Lange Medical Publications, Los Altos, Calif. (1988)) are considered to be associated with biobehavioral factors (Weiner, H., PSYCHOBIOLOGY AND HUMAN DISEASE, Elsevier, N.Y. (1977); Ader et al., supra). In this example, patients suffering from an autoimmune disease are selected. These patients have diseases including myasthenia gravis, multiple sclerosis, systemic lupus erythematosus, autoimmune thyroiditis (Hashimoto's thyroiditis), Graves' disease, inflammatory bowel disease, autoimmune uveoretinitis, polymyositis and certain types of diabetes. These patients are subjected to stress including common behavioral stress (such as an oral mathematical test) or a cold pressor test, known to be associated with increases in catecholamine levels and increases in heart rate. The levels of salivary cytokines are determined as above. Salivary IL-1 and IL-2 are elevated both in anticipation of and during the course of stress. These changes in cytokines can be correlated with disease symptoms and generate useful predictors for onset of these symptoms.

EXAMPLE IX
Comparison of Cytokine From Saliva With a Standard Cytokine

A saliva sample that registered approximately 100 ng/ml was lyophilized and re-constituted in one-tenth is original volume (so the theoretical conc was 1 ug/ml). 100 ul of this solution was injected onto an isocratic high performance liquid chromatograph (HPLC), using a gel filtration sizing column (Zorbax GF-250, DuPont, Wilmington, DE), which had been equilibrated with 100 ug BSA/ml in 100 mM NaHPO$_4$ buffer. Eluted 500 ul fractions were collected each minute.

Following this run, IL-2 standard (10 ug/ml) was injected onto the column. Identical to that described above, 100 ul of this solution was injected, and fractions collected. All samples were frozen at −20° C. until assayed by EIA.

The IL-2 EIA was performed as per ARI's instructions, using 50 ul samples for standards and unknowns. Each plate contained its own standard curve, and all samples were analyzed on the same day. The resultant ODs were extrapolated from their respective standard curve to give a potency estimate.

Figure 21:
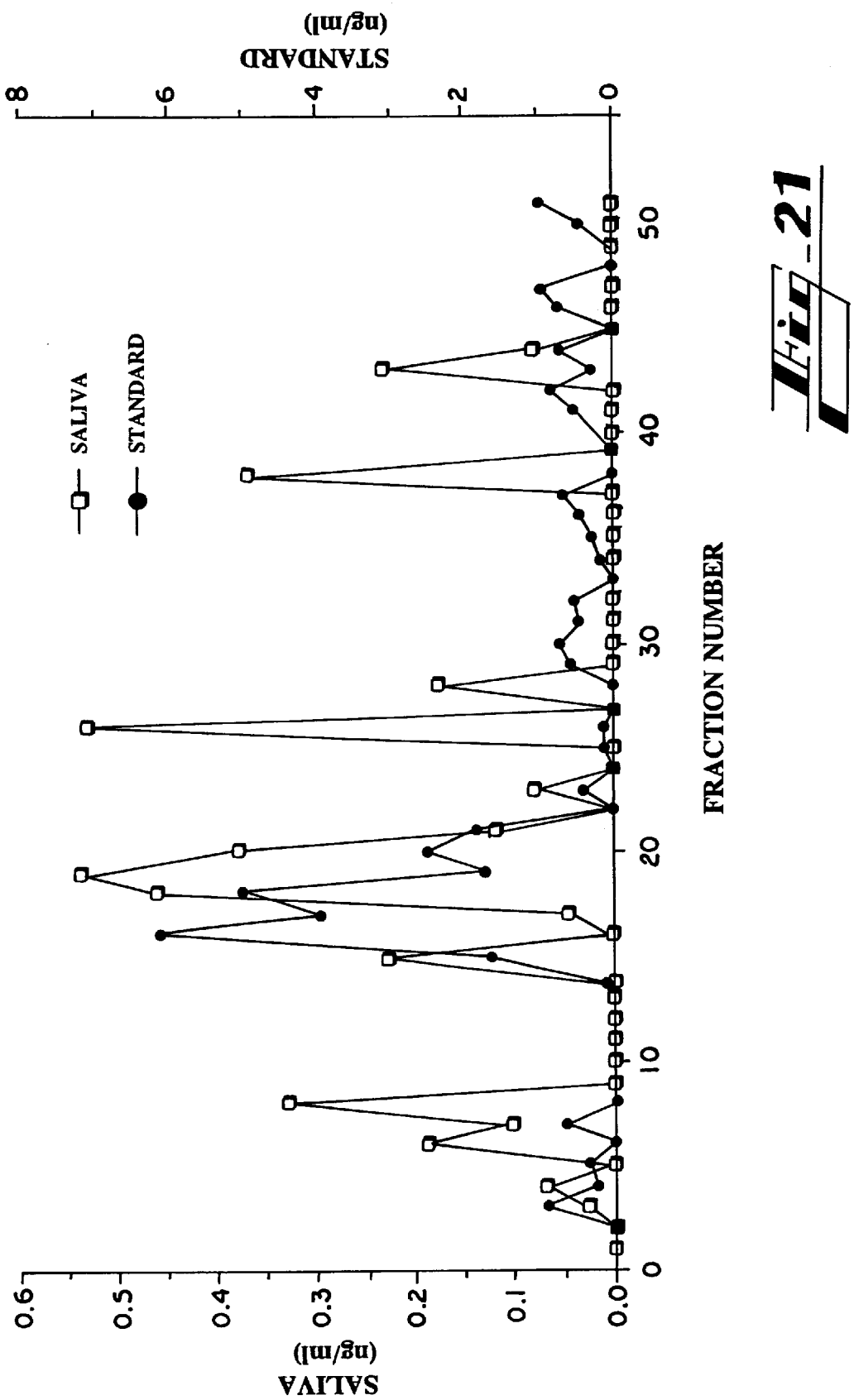
FIG. 21 shows HPLC separation of IL-2 immunoreactivity in saliva and an IL-2 standard.

The data are presented in FIG. 21. The concentrations of IL-2 immunoreactivity are depicted on the y-axis and the fraction numbers are represented on the x-axis. As can be seen from this figure, the quantity of IL-2 in the saliva sample and in the standard are different. This difference is due to the one-tenth concentration of IL-2 in saliva compared to the standard solution.

The chromatograms show clear immunoreactivity (defined by 3 sequentially elevated samples) in the same position (fraction numbers 15 through 22). Also, note the coincident immunoreactivity throughout the two chromatograms. It appears that IL-2 measured in saliva is similar to standard IL-2.

EXAMPLE X
Method and Mathematical Presentation of a Cytokine Clinical Diagnostic Cytokines are the hormones of the immune system. Ample evidence has shown that unique, specific proteins are secreted by the various cellular elements of the immune system to regulate immune function. This regulation oftentimes takes the form of increased cell growth of specific cellular elements of the immune system. For example, the cytokine interleukin-2 (IL-2) stimulates T helper cell type 1 cell growth, which is responsible for the cellular immune response, while IL-4 and IL-10 stimulates T helper cell type 2 cell growth, which increases the humoral (antibody) response.

Monitoring the cytokine state of an individual's biological fluid is useful for assessing the clinical status of an individual. Determining the amount of substantially all (total) of the cytokine in biological fluids is accomplished with the competitive immunoassay as described above. This system is not restricted by specific cytokine epitopes for capture or detection. Thus, the system measures substantially all cytokine, both that which is free (free cytokine), and that which is bound to binding or masking proteins (bound cytokine). The sum of free cytokine plus bound cytokine represents the total cytokine in a biological fluid.

Measurement of the free fraction is accomplished by a non-competitive sandwich-type immunoassay. This immunoassay system relies upon the capture (or trapping) of the analyte by an immobilized antibody, followed by the addition of a second (detection) antibody. The capture antibody may be a monoclonal or polyclonal antibody, and the detection antibody may also be a monoclonal or polyclonal antibody. The detection antibody provides the detection signal, either through its species specificity, so that a secondary labelled antibody may be used to detect the detection antibody or its being labelled with a detection molecule itself. Such detection molecules may be, but are not limited to, a radioactive isotope, such as $I^{125}$, an enzyme, such as alkaline phosphatase, or biotin. Because of steric hindrance or cytokine epitope masking by binding proteins the non-competitive sandwich-type immunoassay detects predominantly only the free cytokine fraction.

The present invention encompasses the use of both immunoassay technologies to measure both the free and the total cytokine levels in a biological fluid. Determining the ratio of free cytokine to total cytokine is an accurate description of the clinical status of an individual for that specific cytokine. Mathematically, the ratio is the free cytokine times a constant (K) divided by the total cytokine. This is the Cytokine Index (CI) for a specific cytokine. More particularly, the invention relates to a method of monitoring cytokine states in a biological fluid comprising, the steps of determining the ratio of free cytokine to total cytokine in a biological fluid, wherein the free cytokine is the amount of cytokine detectable in a non-competitive sandwich-type immunoassay, and wherein total cytokine is the amount of cytokine detectable in a competitive immunoassay.

The present invention also relates to a method of comparing the Cytokine Indexes of a plurality of cytokines to assess the clinical status of an individual. For example, the CI for IL-2 is compared to that for IL-10 to generate a CI ratio. The CI ratio in this example is an index of Th1 to Th2 function as determined by the functionality of the two subsets of T cell functionality of different components of the immune system. The CI ratio is diagnostic for specific clinical presentations, and is used diagnostically, as well as the CI alone. The CI or the CI ratio are clinical diagnostics for such illnesses as autoimmune diseases, including rheumatoid arthritis, immunodeficiency diseases, such as acquired immunodeficiency syndrome (AIDS), transplantation rejection, or cancer therapy. These diagnostics are not limited to these specific conditions. More particularly, the invention relates to a method of monitoring cytokine states in a biological fluid comprising, the steps of determining the cytokine index for a first cytokine by comparing the ratio of free first cytokine to total first cytokine in a biological fluid, wherein the free first cytokine is the amount of first cytokine detectable in a non-competitive sandwich-type immunoassay, and wherein total first cytokine is the amount of first cytokine detectable in a competitive immunoassay; determining the cytokine index for a second cytokine by comparing the ratio of free second cytokine to total second cytokine in a biological fluid, wherein the free second cytokine is the amount of second cytokine detectable in a non-competitive sandwich-type immunoassay, and wherein total second cytokine is the amount of second cytokine detectable in a competitive immunoassay; and comparing the cytokine index for the first cytokine with the cytokine index for the second cytokine.

Having now fully described this invention, it will be appreciated by those skilled in the art that the same can be performed within a wide range of equivalent parameters, concentrations and conditions, without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention, and including such departures from the present disclosure as come within known or customary practice within the art to which the invention pertains, and as may be applied to the essential features hereinbefore set forth as follows in the scope of the appended claims.

We claim:

1. A method for detecting the concentration of free cytokine in a biological sample comprising the following steps in any order:

(1) measuring the total amount of cytokine in a first portion of the sample with a competitive immunoassay comprising an antibody that binds specifically to substantially all of the cytokine in the sample, whether free or bound to a carrier molecule, wherein the antibody is immobilized on a solid phase support;

(2) measuring the free cytokine in a second portion of the sample with a sandwich immunoassay, wherein the free cytokline is a fraction of the total cytokine.

2. The method of claim 1, wherein the cytokine concentrations of two or more cytokines are determined.

3. The method of claim 1, wherein the cytokine is selected from the group consisting of interleukin-1α, interleukin-1β, interleukin-2, interleukin-6, interferon-α, interferon-gamma, and tumor necrosis factor.

4. The method of claim 1, wherein the antibody of the competitive immunoassay is polyclonal.

5. The method of claim 1, wherein the antibody of the competitive immunoassay is monoclonal.

6. The method of claim 1, wherein the biological sample is selected from the group consisting of blood, saliva, nasal secretions, tears, urine, lymphatic fluid, cerebrospinal fluid, mucous, mammary secretions, and synovial fluid.

* * * * *